(12) United States Patent
Hampe et al.

(10) Patent No.: US 8,814,107 B2
(45) Date of Patent: Aug. 26, 2014

(54) FASTENING DEVICE, MEDICAL INSTRUMENT AND INSTRUMENT SYSTEM WITH SUCH A FASTENING DEVICE

(75) Inventors: Markus Hampe, Lübeck (DE); Holger Stegmann, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 709 days.

(21) Appl. No.: 12/478,341

(22) Filed: Jun. 4, 2009

(65) Prior Publication Data
US 2009/0302178 A1    Dec. 10, 2009

(30) Foreign Application Priority Data
Jun. 5, 2008   (DE) .......................... 10 2008 026 989

(51) Int. Cl.
| | |
|---|---|
| F16L 3/00 | (2006.01) |
| A47B 96/06 | (2006.01) |
| B25G 3/20 | (2006.01) |
| F16M 11/04 | (2006.01) |
| F16M 11/24 | (2006.01) |
| F16M 11/42 | (2006.01) |
| A61M 16/00 | (2006.01) |
| A61M 16/10 | (2006.01) |
| A61M 16/16 | (2006.01) |

(52) U.S. Cl.
CPC ......... *F16M 11/04* (2013.01); *F16M 2200/028* (2013.01); *F16M 11/24* (2013.01); *A61M 16/0051* (2013.01); *A61M 16/10* (2013.01); *F16M 11/42* (2013.01); *A61M 2209/082* (2013.01); *A61M 16/16* (2013.01); *A61M 2209/084* (2013.01)
USPC ...................... 248/121; 248/122.1; 248/218.4; 248/220.21; 248/223.41; 248/227.3; 248/689; 248/229.1; 248/229.22; 248/228.3; 248/230.3; 248/231.41; 248/316.4; 248/228.1; 403/374.1; 403/374.2; 403/374.3; 403/374.4; 403/338; 403/381

(58) Field of Classification Search
USPC ......... 248/121, 122.1, 218.4, 220.21, 223.41, 248/354.3, 125.1, 227.3, 187.1, 224.61, 248/205.1, 297.21, 689, 229.1, 229.12, 248/229.22, 228.3, 230.3, 231.41, 316.4; 403/374.1–374.4, 338, 381; 108/50.01; 52/36.3
See application file for complete search history.

(56) References Cited

U.S. PATENT DOCUMENTS

| | | | | |
|---|---|---|---|---|
| 1,658,956 | A | * | 2/1928 | Wehr ............................ 104/111 |
| RE17,629 | E | * | 3/1930 | Wehr ............................ 104/111 |

(Continued)

FOREIGN PATENT DOCUMENTS

| | | |
|---|---|---|
| EP | 0 321 120 B1 | 6/1989 |
| EP | 0387011 A2 | 9/1990 |

(Continued)

*Primary Examiner* — Terrell McKinnon
*Assistant Examiner* — Christopher Garft
(74) *Attorney, Agent, or Firm* — McGlew and Tuttle, P.C.

(57) ABSTRACT

A fastening device (3) for detachably fastening a medical instrument (2A-2E) to a holding structure (1) includes two crossbeams (4A, 4B), two longitudinal beams (5A, 5B) with a claw (6) for extending behind a holding surface (1A) of the holding structure. A guide (7-9) is provided, by which the crossbeams (4A, 4B) are moved in the direction of the claws (6) of the longitudinal beams during a motion of the longitudinal beams (5A, 5B) in relation to one another. A clamping structure (12) is provided for moving the longitudinal beams (5A, 5B) in relation to one another.

23 Claims, 13 Drawing Sheets

(56) References Cited

U.S. PATENT DOCUMENTS

| | | | | |
|---|---|---|---|---|
| 1,768,543 | A * | 7/1930 | Clausing | 248/228.3 |
| 1,974,628 | A * | 9/1934 | Donald | 248/228.3 |
| 3,465,995 | A * | 9/1969 | Whitman | 248/228.3 |
| 5,813,641 | A * | 9/1998 | Baldwin | 248/223.41 |
| 6,246,905 | B1 | 6/2001 | Mogul | |
| 6,251,113 | B1 | 6/2001 | Appelbaum et al. | |
| 6,626,445 | B2 * | 9/2003 | Murphy et al. | 280/47.34 |
| 6,695,524 | B2 * | 2/2004 | Monson et al. | 403/374.3 |
| 6,736,564 | B2 * | 5/2004 | Loerch | 403/35 |
| 6,799,744 | B1 * | 10/2004 | Koistinen | 248/227.3 |
| 7,178,765 | B2 * | 2/2007 | Huang | 248/122.1 |
| 7,367,571 | B1 | 5/2008 | Nichols | |
| 7,708,237 | B2 * | 5/2010 | Mummert et al. | 248/122.1 |
| 7,748,676 | B2 * | 7/2010 | Huang | 248/276.1 |
| 2003/0201697 | A1 | 10/2003 | Richardson | |
| 2004/0047683 | A1 * | 3/2004 | Loerch | 403/381 |
| 2004/0227443 | A1 | 11/2004 | Sandoval | |
| 2004/0262867 | A1 * | 12/2004 | Arceta et al. | 280/47.35 |
| 2005/0178298 | A1 * | 8/2005 | Rossini | 108/50.01 |
| 2005/0206107 | A1 * | 9/2005 | Schubert et al. | 280/79.11 |
| 2005/0236530 | A1 * | 10/2005 | Weatherly et al. | 248/122.1 |
| 2006/0071581 | A1 | 4/2006 | Harvey | |
| 2007/0218769 | A1 * | 9/2007 | Mummert et al. | 439/630 |
| 2007/0228680 | A1 * | 10/2007 | Reppert et al. | 280/47.35 |
| 2008/0121769 | A1 * | 5/2008 | Redecker | 248/220.21 |

FOREIGN PATENT DOCUMENTS

| | | |
|---|---|---|
| EP | 0675571 A1 | 10/1995 |
| GB | 2282638 A | 4/1995 |
| WO | WO 98/47409 A1 | 10/1998 |
| WO | WO 2008/067428 A1 | 6/2008 |

* cited by examiner

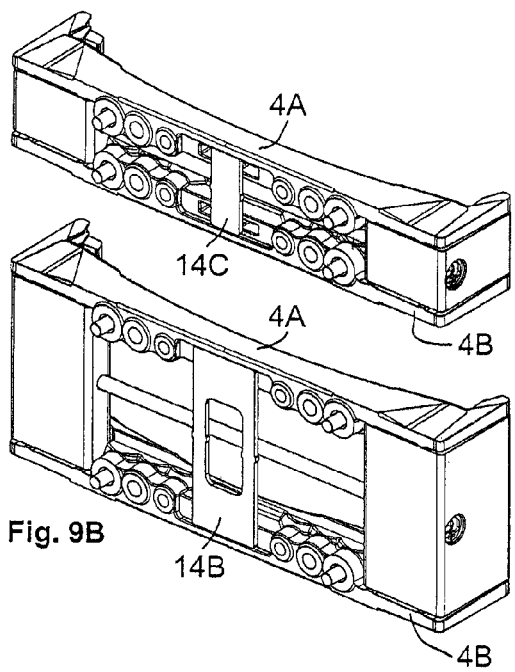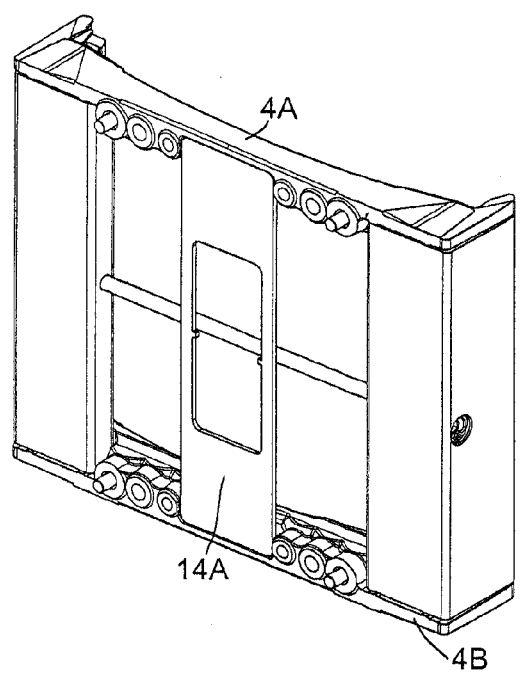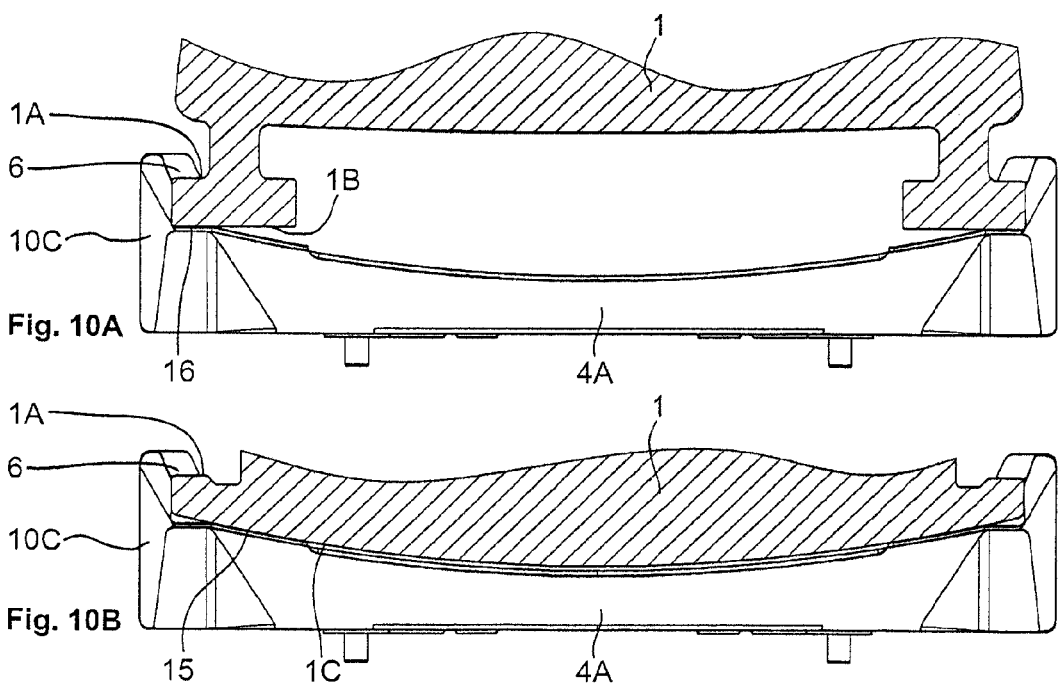

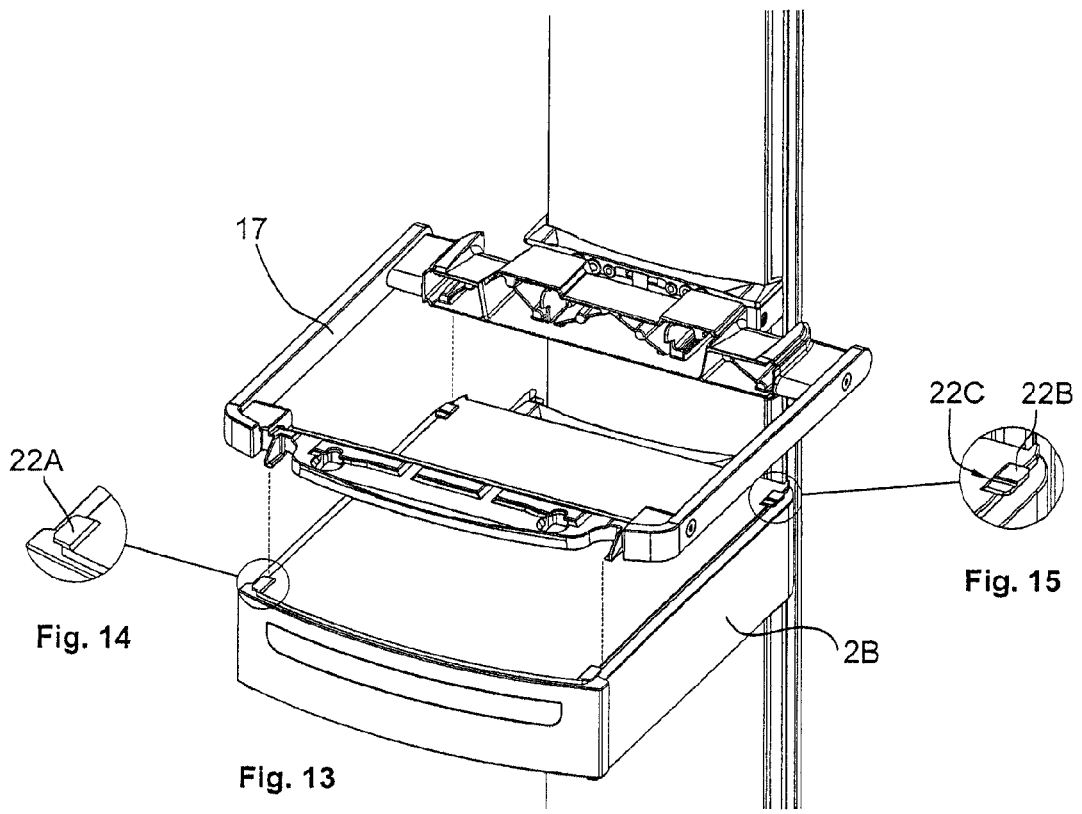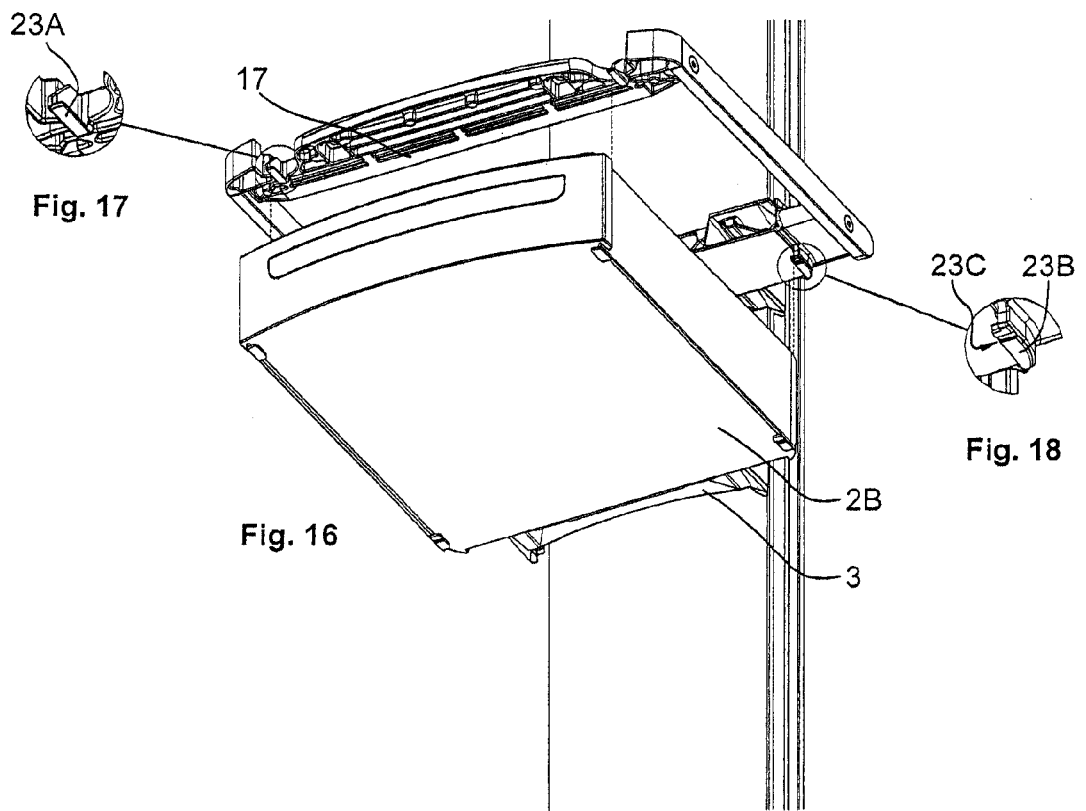

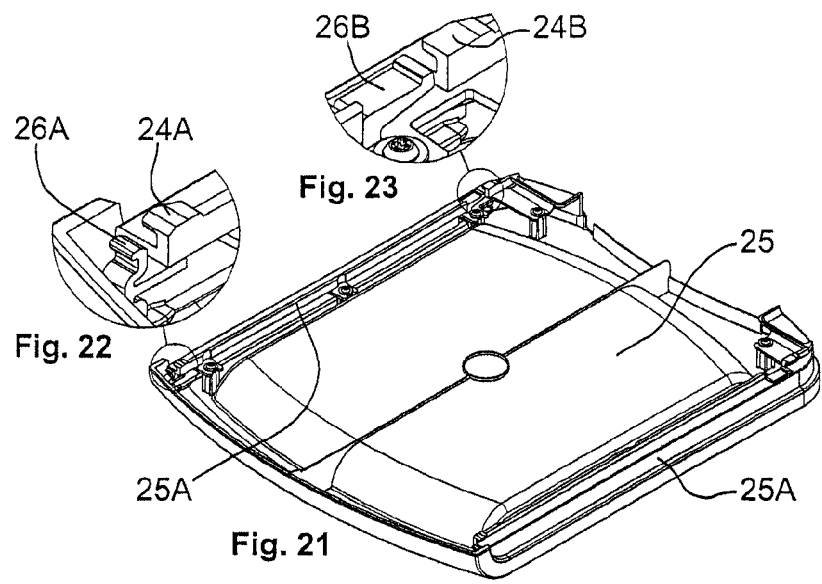
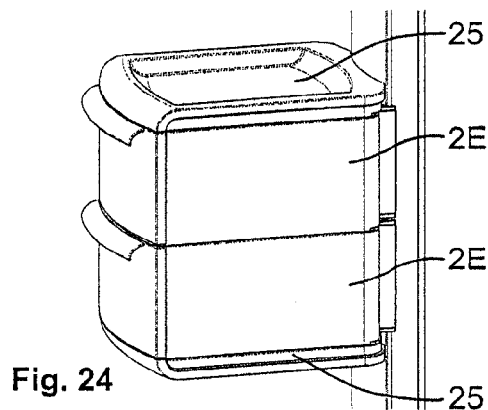
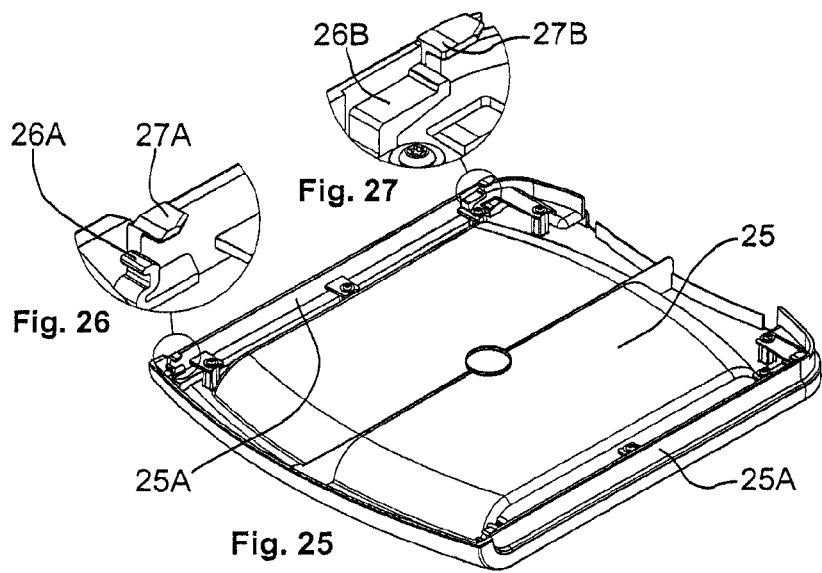

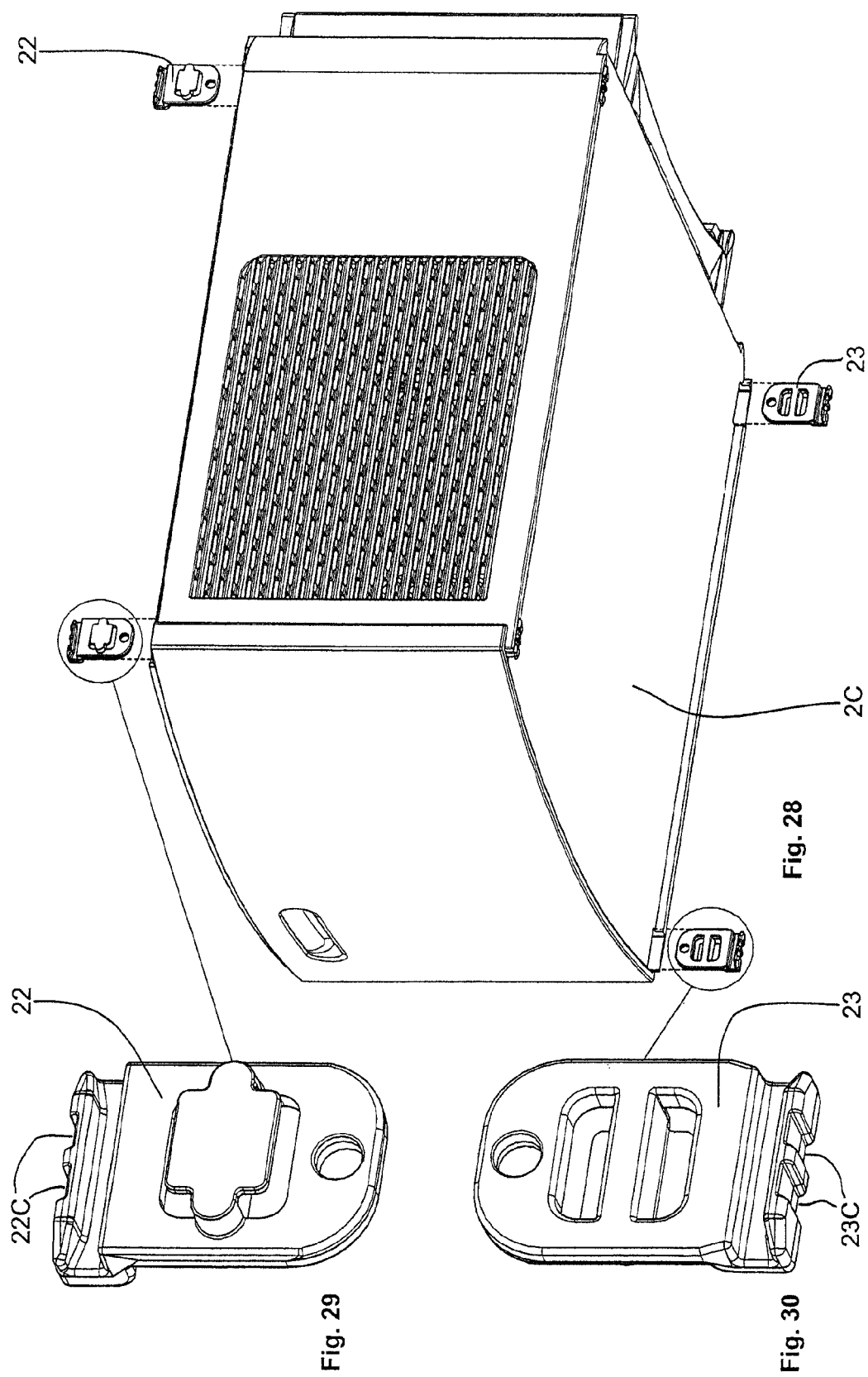

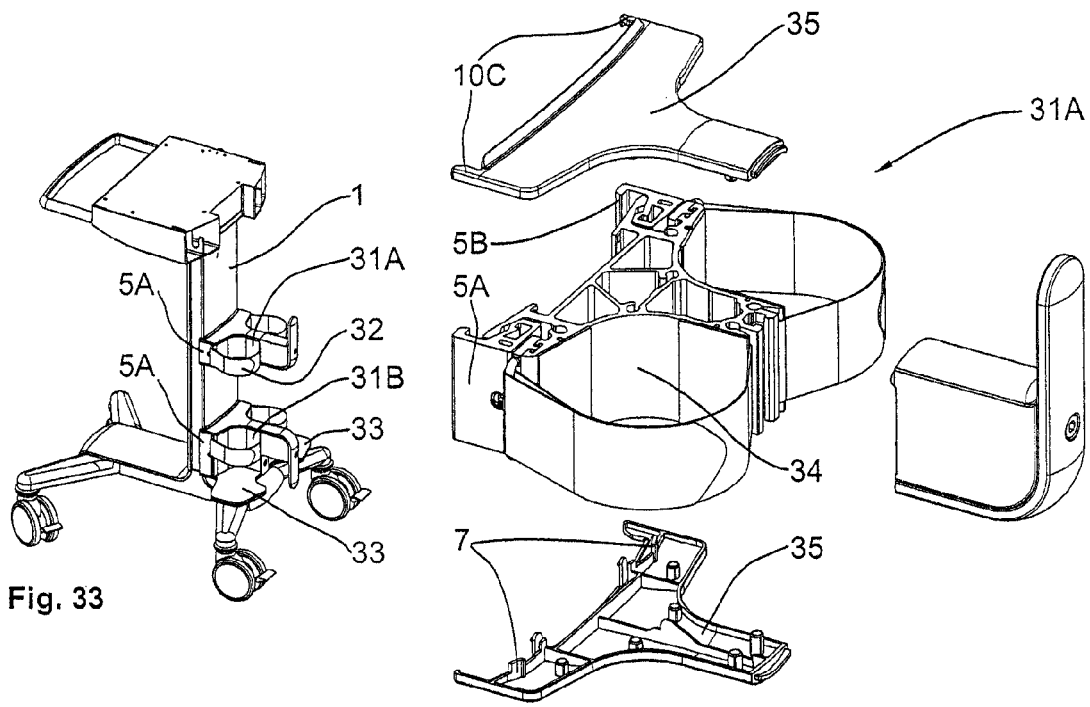
Fig. 33
Fig. 34
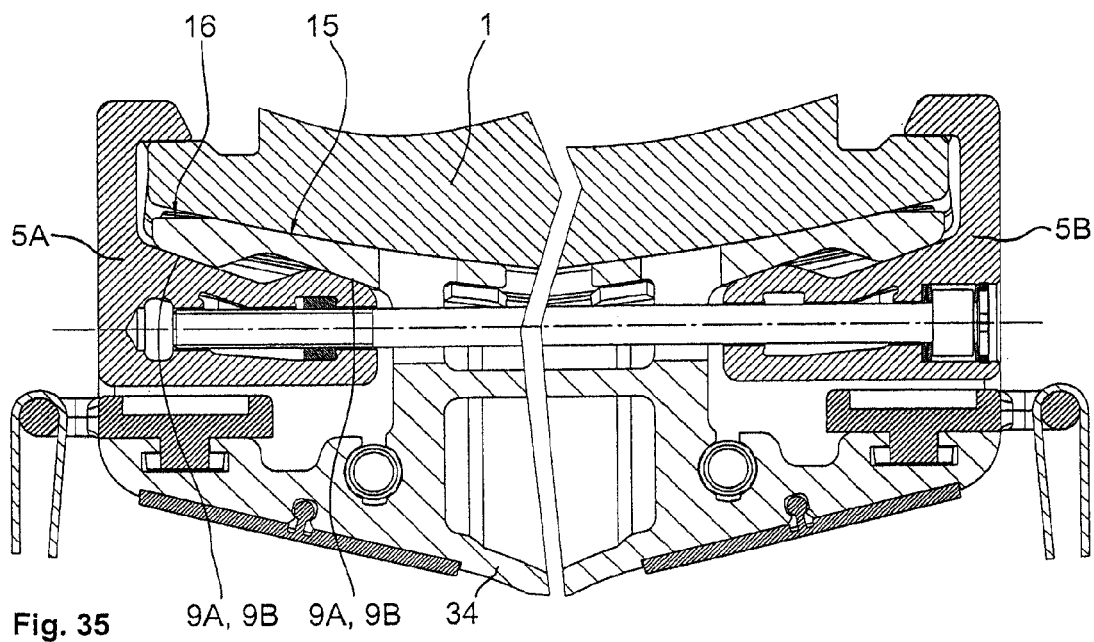
Fig. 35

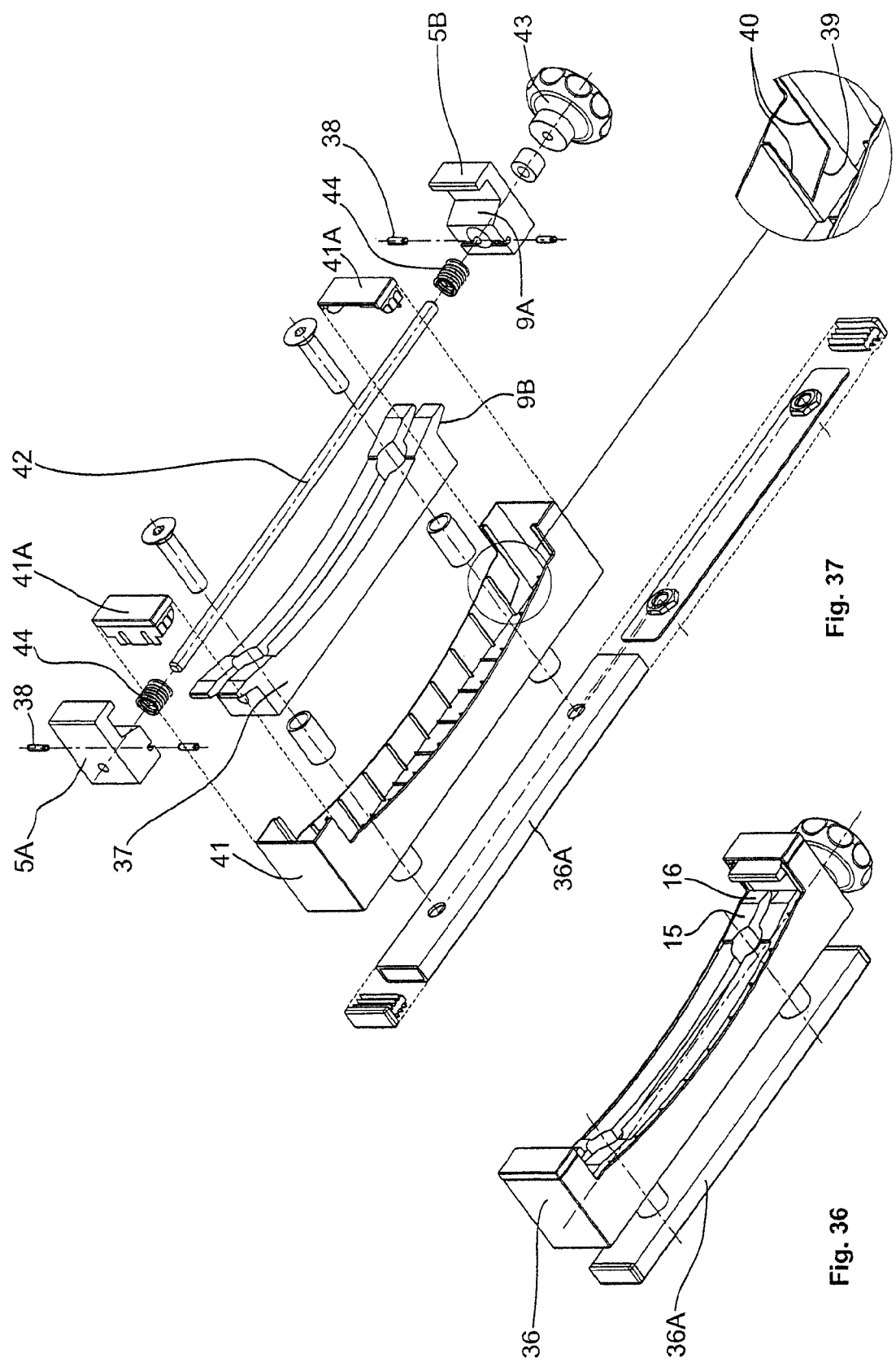

FASTENING DEVICE, MEDICAL INSTRUMENT AND INSTRUMENT SYSTEM WITH SUCH A FASTENING DEVICE

CROSS REFERENCE TO RELATED APPLICATIONS

This application claims the benefit of priority under 35 U.S.C. §119 of German Patent Application DE 10 2008 026 989.1 filed Jun. 5, 2008, the entire contents of which are incorporated herein by reference.

FIELD OF THE INVENTION

The present invention pertains to a fastening device for detachably fastening a device, especially a medical instrument, to a holding structure, as well as to a medical instrument and to an instrument system with such a fastening device.

BACKGROUND OF THE INVENTION

It is known in medical engineering that medical instruments are fastened detachably to a holding structure, for example, a ceiling supply unit in an intensive care unit or to a vertical column of a trolley. This makes possible a modular design of an instrument system with different medical instruments, where individual instruments can be replaced, added and/or removed according to need.

EP 0 321 120 B1 proposes a fastening device with a clamp and with a frame, which can be fastened thereto in different positions and in which the medical instrument is in turn held in different angular positions, for the detachable fastening of the individual medical instruments to a tubular holding structure. A claw of the clamp extends around the tubular holding structure and is fixed to the holding structure by a clamping screw in a frictionally engaged manner. However, the flow of force in this fastening device is not optimal. To fix the medical instruments, some of which are heavy, reliably and without clearance, correspondingly strong frictional and hence normal forces are required. The entire normal force is introduced at two mutually opposite action sites in the fastening device according to EP 0 321 120 B1, which leads to high load on the holding structure and to high overturning moments.

SUMMARY OF THE INVENTION

One object of the present invention is therefore to make available a fastening device for detachably fastening a device, especially a medical instrument, to a holding structure, as well as a medical instrument and an instrument system with improved flow of force.

A fastening device for detachably fastening a device, especially a medical instrument, to a holding structure according to the present invention comprises one or two or more crossbeams and at least two longitudinal beams with altogether at least one claw for extending behind a holding surface of the holding structure. The longitudinal beams preferably extend in the longitudinal direction of the holding structure, especially of the holding surfaces thereof. The crossbeams are oriented, again preferably, essentially at right angles thereto. The holding surfaces of the holding structure may be formed, for example, by undercuts or L- or T-shaped webs.

The crossbeams and longitudinal beams are coupled with one another by a guide, by which the crossbeam or crossbeams is/are moved in the direction of the claws of the longitudinal beams during a motion of the longitudinal beams relative to one another. The guide preferably permits a motion of the longitudinal beams relative to one another in the direction in which the crossbeams extend, i.e., essentially at right angles to the holding structure. The motion that moves the crossbeams in the direction of the claws of the longitudinal beams may equally be a motion of the longitudinal beams away from one another or towards one another. The present invention also covers an embodiment in which only one of the longitudinal beams moves relative to the other. A distance between the longitudinal beams is changed now. It may be increased or decreased.

During the relative motion, the crossbeams or crossbeam are also moved, in a restrictedly guided manner, in the direction of the claws of the longitudinal beams, i.e., towards clamping surfaces of the holding structure, which are located opposite the holding surfaces, behind which they extend, in the direction of motion of the crossbeams. The crossbeams and longitudinal beams, which are moving towards each other, thus clamp the holding surfaces and the opposite clamping surfaces of the holding structure between them and fix the fastening device at the holding structure in a frictionally engaged manner. A means, especially a clamping means, by which the longitudinal beams can be moved relative to one another, is provided for this.

After the claws and crossbeams have made contact with the holding structure, they can be braced against each other by the clamping means, which can impose for this a prestressing force on the longitudinal beams in the direction of motion thereof relative to one another. The normal forces applied by the clamping means between the holding surfaces and the claws or between the clamping surfaces and the crossbeams generate corresponding frictional forces, which fix the fastening device at the holding structure in a frictionally engaged manner.

Frictional and normal forces can thus advantageously be distributed by the one clamping means among four action sites between the two crossbeams and the two clamping surfaces of the holding structure, which said clamping surfaces are located opposite the holding surfaces (or at least between two action sites in case of the design with only one crossbeam). This improves the flow of force between the fastening device and the holding structure. The load on the components can be reduced and/or the safety of fastening can be increased hereby. In particular, the components may be designed as weaker components and thus they can be dimensioned as lighter and/or more cost-effective components.

The claws can be preferably meshed and unmeshed with the holding surfaces of the holding structure by the motion of the longitudinal beams relative to one another. Due to the motion of the longitudinal beams relative to one another, the holding surfaces are thus gripped from behind or released at the same time and the crossbeams are fed together or moved apart, so that the holding structure is clamped between the crossbeams and longitudinal beams or released by these. This makes it possible to place the fastening device from the front on the holding structure. If the longitudinal beams are then moved relative to one another, their claws extend behind the holding surfaces of the holding structure, so that the fastening device is guided in the direction of the longitudinal beams. For removal, the longitudinal beams are moved in the opposite direction relative to one another, so that clamping is first released and the claws will then release the holding surfaces. The fastening device can subsequently be lifted off from the holding structure in the forward direction. A fastening device according to the present invention thus has improved handling.

The guide may comprise a surface pair with a wedge surface arrangement formed on the longitudinal beams and a complementary wedge surface arrangement formed on the crossbeams, where wedge surfaces of the wedge surface arrangement and complementary wedge surface arrangement that touch each other form an angle with the direction of motion of the longitudinal beams relative to one another.

If the longitudinal beams are being moved relative to one another, the complementary wedge surfaces run up onto the wedge surfaces. Due to the angle in relation to the direction of motion of the longitudinal beams, a motion of the longitudinal beams relative to one another will then bring about at the same time a motion of the crossbeams at right angles hereto and thus performs the feed motion of the crossbeams. After the crossbeams have come into contact with the clamping surfaces of the holding structures, the clamping means imposes a normal force between the clamping surfaces and the crossbeams, which can be boosted by the wedge effect. The angle is advantageously between 5° and 40°, preferably between 10° and 30° and especially preferably between 12° and 20°.

The force exerted by the clamping means on the longitudinal beams preferably acts centrally on the wedge surfaces. This advantageously counteracts a self-locking of the running-up motion between the wedge surface and the complementary wedge surface. An overturning moment acting on the longitudinal beams can also be reduced or avoided by the essentially central introduction of force onto the wedge surface.

To further reduce or prevent such an overturning moment, the wedge surfaces may also be of a multipart design, in which case the individual partial wedge surfaces are preferably spaced far apart from each other.

In addition or as an alternative to the surface pairing, the guide may comprise a tongue-and-groove mimic with a projection arranged on one assembly formed by a longitudinal beam and the crossbeams, a so-called tongue, and a recess formed on the other assembly formed by the longitudinal beam and crossbeams, a so-called groove, wherein the groove and tongue form an angle with the direction of motion of the longitudinal beams relative to one another. The angle is advantageously between 5° and 40°, preferably between 10° and 30° and especially preferably between 12° and 20°.

A tongue may be formed on a crossbeam and mesh with a corresponding groove in a longitudinal beam. In addition or as an alternative, a tongue may be formed on a longitudinal beam and mesh with a corresponding groove in a crossbeam.

Such a tongue-and-groove mimic advantageously also forms end stops for the motion of the longitudinal beams relative to one another.

The guide preferably comprises both a surface pairing and a tongue-and-groove mimic. The angles, wedge surfaces and complementary wedge surfaces as well as groove and tongue advantageously essentially agree with the direction of motion of the longitudinal beams in this case. Jamming or self-locking between the surface pairing and the tongue-and-groove mimic can thus be avoided.

To avoid jamming, it is advantageous to design the tongue-and-groove mimic with a clearance.

A path reserve, which permits an additional motion of the longitudinal beams relative to one another when the longitudinal beams and crossbeams are in contact with the holding structure, is advantageously provided in the guide, so that the clamping means can brace the longitudinal beams and crossbeams in relation to one another regardless of manufacturing-related dimensional variations and it can clamp the holding structure between these.

The clamping means is preferably accessible laterally in order to move the longitudinal beams in relation to one another. The clamping means may comprise for this, for example, a bolt, which passes through the longitudinal beams essentially in the direction of motion thereof. An external thread of the bolt can cooperate with an internal thread of a longitudinal beam, so that the position of the bolt in relation to this longitudinal beam changes by rotating the bolt about its longitudinal axis. A corresponding torque can be applied to a bolt head located on the outside, for example, a screw head, or a hexagon socket. Handling of the fastening device is simplified hereby. Instead of a bolt, it is also possible to provide a thread rod and a screw grip with internal thread, so that the holding structure can be fastened and released without a tool when this is desirable.

The fastening device may comprise a positioning means for positioning the fastening device at the holding structure. The positioning means may comprise, for example, one or more projections, which can mesh with corresponding recesses in the holding structure. In addition or as an alternative, the positioning means may comprise one or more recesses, which can be meshed with by corresponding projections on the holding structure. Mounting of the fastening device can be facilitated hereby. The projections can be preferably fastened detachably to the fastening device or the holding structure, so that they are arranged only when needed and in different positions. Fastening in other positions is thus likewise possible by the detachable projections not being arranged or being arranged at another site.

The crossbeams may be designed as identical shaped parts, which lowers the manufacturing and stocking costs. They may be fastened to the medical instrument detachably, for example, by means of screws, locking and/or plug-in connections, or nondetachably, for example, by means of bonding, welding or the like. In particular, the crossbeams may be able to be fastened to the medical instrument laterally or, preferably, on the rear side. In another embodiment with only one crossbeam, this may be preferably manufactured from an extruded section.

The contour of the crossbeams is preferably adapted to the contour of the clamping surfaces and is, in particular, complementary hereto in such a way that it is complementary to different clamping surfaces of different holding structures. This makes it possible to fasten the fastening device or the medical instrument connected thereto to different holding structures.

At least one crossbeam preferably has at least one centering flank, which is in contact with the holding structure in a positive-locking manner and limits a displacement of the fastening device in the direction of motion of the longitudinal beams in relation to one another when this crossbeam touches the clamping surface. The fastening device can be positioned as a result relative to the holding structure in this direction. At least one crossbeam advantageously has two centering flanks, which are located opposite each other and are each in contact with the holding structure in a positive-locking manner, limit displacement of the fastening device in both directions of motion and thus position, especially center, the fastening device in relation to the holding structure.

The longitudinal beams may be designed as identical shaped parts, especially extruded parts, which lowers the manufacturing and stocking costs.

The longitudinal beams can be preferably connected detachably to the crossbeams. In particular, the longitudinal beams and crossbeams may be coupled with one another by a plug-in connection, which may be formed, for example, by the tongue-and-groove mimic of the guide. The crossbeams and longitudinal beams especially preferably form a stable assembly unit only when they are plugged together and the crossbeams are fastened to the medical instrument. This facilitates stocking of the fastening device. Due to the elimination of a permanent, separate connection between the crossbeams and longitudinal beams, the fastening device can also have a simpler shape and be manufactured in a simpler manner and/or have a lighterweight design.

The longitudinal beams may be arranged between the crossbeams and space these apart. It is advantageous in this connection to select the longitudinal beams from a plurality of prefabricated longitudinal beams, which have different lengths. This makes it possible to design fastening devices of different heights and thus to adapt these to the particular medical instrument. For example, longitudinal beams may be prefabricated in a standardized series with the lengths of 0.5 h, h, 2 h, . . . , where h is preferably selected to be such that the overall height of the fastening device can be in the range between 60 mm and 100 mm, preferably between 70 mm and 90 mm and especially preferably equal 80 mm. If the particular longitudinal beam with the greatest possible length is selected, corresponding to the height of the medical instrument, a torque resulting from the weight of the instrument can be well supported in the action sites located far apart from one another, whose number equals, for example, two or four.

In particular, when the longitudinal beams are prefabricated in different lengths and are subsequently connected detachably to the crossbeams, the fastening device may comprise a mounting means, at which the two crossbeams can be fastened detachably at different heights. The fastening device can be preassembled in this manner as a semifinished product before it is fastened to the medical instrument.

A fastening device according to the present invention may comprise an intermediate layer, which is located between the crossbeams and the clamping surfaces of the holding structure when the fastening device is connected to the holding structure.

Such an intermediate layer may advantageously increase the coefficient of friction between the crossbeam and the clamping surface and/or protect the surface of the holding structure. In particular, the intermediate layer may be made for this from a plastic. It may be fastened to the crossbeams detachably, for example, by means of screw or plug-in connection, or also nondetachably, for example, by bonding, welding or the like.

The intermediate layer may have the same features as those described above in reference to the crossbeams, which are directly in contact with the clamping surfaces of the holding structure.

Thus, the contour of the intermediate layer can be adapted to the contour of the clamping surfaces and may be designed, in particular, such that it is complementary to different clamping surfaces of different holding structures. In addition or as an alternative, the intermediate layer may have at least one and preferably two centering flanks.

A fastening device according to the present invention may comprise a securing means, which counteracts a change in the spacing between the longitudinal beams in relation to one another. In particular, such a securing means may comprise one or more elastic means, which impose a prestressing force on the longitudinal beams in the direction of their motion in relation to one another. The securing means may be, for example, a corrugated spring plate or one or more plate springs, which are preferably arranged in opposite directions in relation to one another. Such securing means advantageously counteract the release of the bracing of the crossbeams and longitudinal beams by the clamping means based on dynamic loads.

An instrument system according to a design of the present invention comprises a holding structure and one or more medical instruments, wherein at least one medical instrument can be fastened by a fastening device having one or more of the above-described features to the holding structure.

The instrument system preferably comprises a support frame, which can be fastened by a fastening structure having one or more of the above-described features to the holding structure and to which one or two medical instruments can be fastened.

This makes it possible to fasten at first a relatively lightweight, thin support frame to the holding structure. The medical instrument, which is usually heavier and/or higher and can therefore be handled with greater difficulty, can then be supported or fastened in a first step on the support frame and can itself be fastened, in a second, subsequent step, to the holding structure by a fastening structure having one or more of the above-described features. This facilitates the handling of the instrument system during the mounting and removal of individual medical instruments, protects the instruments from falling down during mounting and removal, and, moreover, increases the stability of the overall system by the additional connection between the support frame and the medical instrument.

The support frame is preferably composed of multiple parts comprising a front part, a rear part and two side parts. By means of side parts of different lengths, it can thus be adapted to medical instruments of different depths and can be correspondingly used in a versatile manner.

A medical instrument according to one embodiment of the present invention has a fastening device with one or more of the above-described features for fastening to a holding structure.

According to a preferred embodiment, a medical instrument has a hook arrangement for fastening to another medical instrument, a support frame or a closing element. This increases the stability of the entire arrangement. Moreover, the medical instrument can be connected by the hook arrangement to the additional medical instrument, the support frame or the closing element rapidly, simply and especially without an additional tool, which simplifies the mounting of the instrument system.

The hook arrangement may comprise hooks on the top side and/or the underside of the medical instrument, and hooks on the top side of a medical instrument of an instrument system according to the present invention may advantageously cooperate with hooks on the underside of another medical instrument of the instrument system according to the present invention, so that different medical instruments can be stacked one on top of another or hung on one another in any desired order and connected to the holding structure. Cooperating hooks may be preferably formed here by a hook-shaped projection and a corresponding recess, with which the hook-shaped projection can mesh.

If an instrument system according to the present invention comprises a support frame and/or a closing element, it is advantageous if the support frame or closing element also has corresponding hooks in order to be connected to medical instruments.

The support frame preferably has corresponding hooks on its top side and underside, the hooks on the top side being able to cooperate with hooks on the underside of a medical instrument and the hooks on the underside being able to cooperate with hooks on the top side of another medical instrument, so that two medical instruments can be connected to the support frame.

Conversely, the closing element shall preferably have an essentially smooth surface without projections or recesses, and be designed, for example, as a depositing tray. The closing element may be of a multipart design for this and have two side parts, which correspond on one side to the hook arrangement on the underside of a medical instrument and on the other side to the hook arrangement on the top side of a medical instrument. Due to corresponding mounting of the side parts on a closing element, the latter will then have a hook arrangement, on the one hand, which corresponds to that on the top side or the underside of a medical instrument and can thus be placed from below on the underside or from the top on the top side of a respective lowermost and uppermost medical instrument. This reduces the manufacturing and stocking costs for the closing elements.

If a medical instrument is connected to another, subjacent medical instrument or support frame, but not to the holding structure itself any longer, this medical instrument would fall down when the additional medical instrument or support frame is detached from its holding structure. A medical instrument therefore comprises in a preferred embodiment a blocking means for blocking a clamping means of a fastening device, by which an additional medical instrument arranged under the medical instrument or a support frame is fastened to the holding structure.

This holding structure may be oriented vertically, horizontally or obliquely in relation to the direction of gravity and designed stationarily, for example, as a ceiling supply unit in an intensive care unit, or in a mobile form, for example, as a trolley.

A medical instrument may be, for example, an anesthesia device or respirator, a monitor, a humidifier, a pressure source, an ultrasound device, an infusion device, a dialyzer, a defibrillator, a power source, for example, a battery, an independent power supply unit or a power pack, a drawer, a test tube or infusion holder, a gas cylinder holder or the like. It is also possible to fasten other, non-medical instruments to a holding structure with a fastening device according to the present invention; in particular, it is possible to fasten a standardized interface, e.g., a standard rail, on which accessories fitting it can in turn be arranged.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 9A is a perspective view showing the fastening device according to the first embodiment of the present invention with a mounting means;

FIG. 9B is a perspective view showing the fastening device according to the first embodiment of the present invention with a mounting means;

FIG. 9C is a perspective view showing the fastening device according to the first embodiment of the present invention with a mounting means;

FIG. 10A is a top cross sectional view showing an instrument system according to a first embodiment of the present invention;

FIG. 10B is a top cross sectional view showing an instrument system according to a first embodiment of the present invention with a modified holding structure;

FIG. 13 is an upper perspective view showing the instrument system according to the first embodiment of the present invention in a third step of mounting;

FIG. 14 is a perspective enlarged detail view indicated by a circle in FIG. 13;

FIG. 15 is a perspective enlarged detail view indicated by a circle in FIG. 13;

FIG. 16 is a lower perspective view showing the instrument system according to the first embodiment of the present invention in the third step of mounting;

FIG. 17 is an enlarged detail view indicated by a circle in FIG. 16;

FIG. 18 is an enlarged detail view indicated by a circle in FIG. 16;

FIG. 21 is an upper perspective view showing a closing element of the instrument system according to the first embodiment of the present invention from the top;

FIG. 22 is an enlarged detail view showing details indicated by a circle in FIG. 21;

FIG. 23 is an enlarged detail view showing details indicated by a circle in FIG. 21;

FIG. 24 is a perspective partial view showing another modified instrument system according to FIG. 1;

FIG. 25 is a lower perspective view showing a closing element of the instrument system according to the modified first embodiment of the present invention from the bottom;

FIG. 26 is an enlarged detail view showing details indicated by a circle in FIG. 25;

FIG. 27 is an enlarged detail view showing details indicated by a circle in FIG. 25;

FIG. 28 is a lower perspective view showing examples of hook geometries for fastening the closing element;

FIG. 29 is an enlarged detail view showing details of an upper hook according to FIG. 28;

FIG. 30 is an enlarged detail view showing details of a lower hook according to FIG. 28;

FIG. 33 is an upper perspective view of a gas cylinder holder fastened to a trolley by means of the fastening device according to the present invention;

FIG. 34 is an upper perspective view showing the gas cylinder holder (shown in a removed state) according to FIG. 33;

FIG. 35 is a cross sectional view showing details of the fastening device according to FIGS. 33 and 34;

FIG. 36 is a perspective view showing another use of the fastening device according to the present invention with a standard rail interface for fastening accessories;

FIG. 37 is a perspective exploded view showing the fastening device according to FIG. 36;

DESCRIPTION OF THE PREFERRED EMBODIMENTS

Figure 1A:
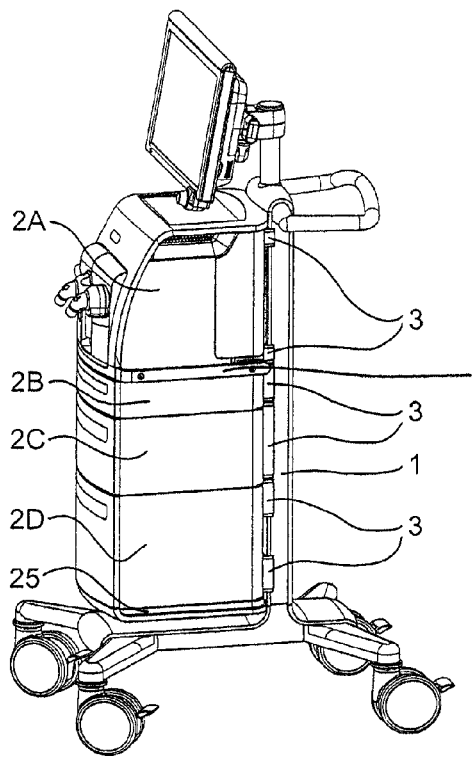
FIG. 1A is a perspective view showing an instrument system according to a first embodiment of the present invention with four medical instruments.

Referring to the drawings in particular, FIG. 1A shows an instrument system according to a first embodiment of the present invention in the form of a trolley.

The trolley comprises a vertical holding structure 1, to which a respirator 2A, a humidifier 2B, a pressure source 2C as well as an independent power supply unit 2D are detachably fastened by means of fastening devices 3. The respirator 2A and humidifier 2B are additionally fastened from the top and from the bottom to a support frame 17, which is likewise fastened detachably to the holding structure 1. A closing element 25 is fastened on the underside of the independent power supply unit 2D.

Figure 1B:
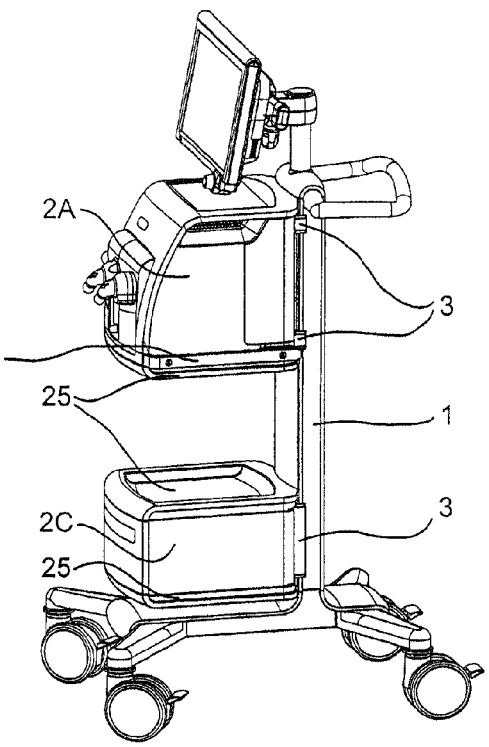
FIG. 1B is a perspective view showing a modified instrument system according to FIG. 1A with two medical instruments.

FIG. 1B shows a modified version of the instrument system according to the first embodiment of the present invention. Based on the configuration shown in FIG. 1A, the humidifier 2B and the independent power supply unit 2D are removed and the pressure source 2C is fastened in another position on the holding structure 1. In addition, additional closing elements 25 are fastened on the underside of the support frame 17 and the top side of the pressure source 2C. The closing element 25 fastened on the top side of the pressure source 2C advantageously forms a depositing tray.

As is apparent from the comparison of FIGS. 1A and 1B, the instrument system according to the first embodiment of the present invention can be modified in a simple manner and adapted to the particular needs by adding and removing individual medical instruments 2 as well as by arranging the existing medical instruments 2 in different positions on the holding structure 1. This shows the advantageous possibility of a modular instrument system according to the present invention, in which the individual medical instruments can be fixed detachably in different positions on a holding structure.

Figure 2A:
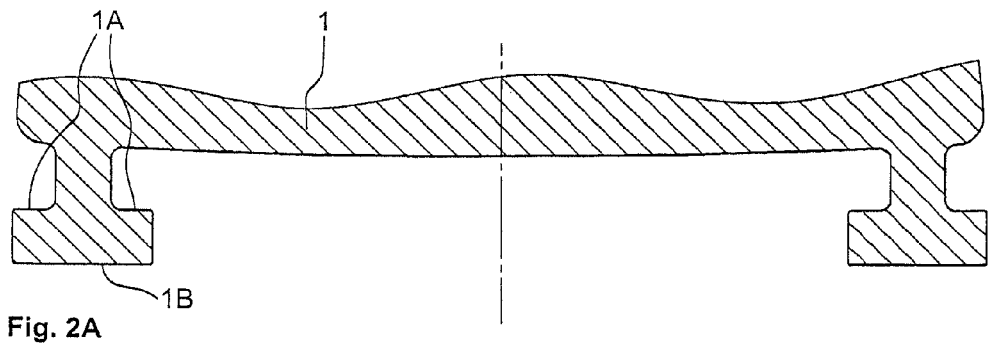
FIG. 2A is a partial cross sectional view showing a of a holding structure of the instrument system according to FIG. 1A.

FIG. 2A shows a partial cross section of the holding structure 1 of the instrument system according to FIGS. 1A and 1B. This holding structure has two T-shaped webs with front clamping surfaces 1B and inner and outer holding surfaces 1A located opposite these.

Figure 2B:
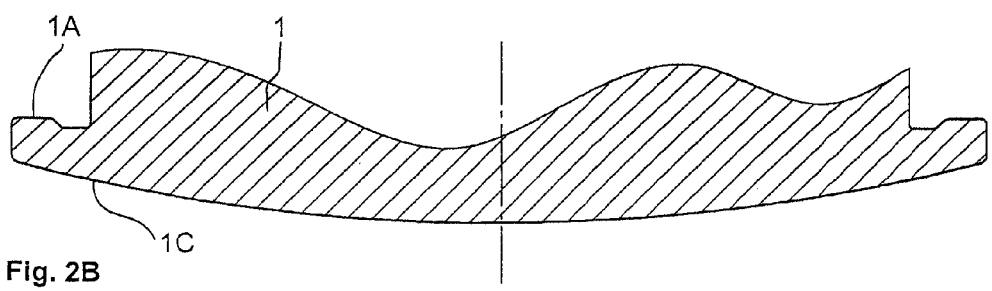
FIG. 2B is a partial cross sectional view showing a modified holding structure of the instrument system according to FIG. 1A.

FIG. 2B shows a partial section of an alternative, preferred holding structure 1 of the instrument system according to FIG. 1A, in which a clamping surface 1C extends cylindrically on the front side (bottom in FIG. 2B) of holding structure 1 and two outer holding surfaces 1A are designed as an undercut.

Figure 3:
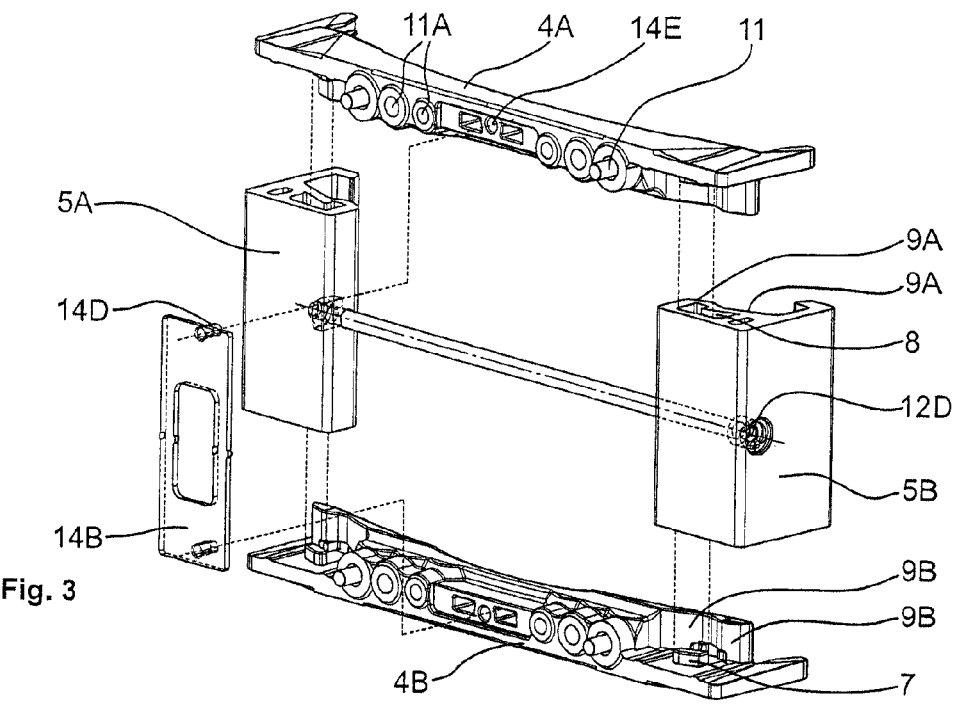
FIG. 3 is an exploded perspective view showing a fastening device according to a first embodiment of the present invention.

FIG. 3 shows an exploded view of a fastening device according to the first embodiment of the present invention, which can be fastened, for example, on the holding structure according to FIG. 2A or according to FIG. 2B and can thus be used in a versatile manner.

It comprises upper and lower crossbeams 4A, 4B, which are designed as identical shaped parts, as well as a left longitudinal beam 5A and a right longitudinal beam 5B, which are manufactured as extruded parts with identical section. On their inner sides, the longitudinal beams 5 have a claw 6 each, with which they can extend behind the outer holding surfaces 1A of the holding structure according to FIG. 2A or 2B (cf. FIG. 4), so that a closed outer side is advantageously obtained.

Oblique projections 7 on the crossbeams 4 and recesses 8 that are complementary hereto in the longitudinal beams 5 form a tongue-and-groove mimic, by which the crossbeams 4 are moved towards the claws 6 of the longitudinal beams in a restrictedly guided manner during a motion of the two longitudinal beams 5 towards one another in the inward direction. At the same time, the tongue-and-groove mimic, which thus acts as end stops, limits the motion of the longitudinal beams in relation to one another in both directions.

The longitudinal beams 5 have two-part wedge surfaces 9A, which run up on corresponding complementary wedge surfaces 9B of the crossbeams 4 and move these likewise in the direction of the claws 6 during a motion of the longitudinal beams 5 towards one another in the inward direction. Wedge surfaces and complementary wedge surfaces together form two surface pairs 9, whose angle in relation to the direction of motion of the longitudinal beams 5 in the inward direction (left-right in FIG. 4) corresponds to the angle of the tongue-and-groove mimic.

On their side facing the respective clamping surfaces 1B and 1C, a respective left-side and right-side intermediate layer 10 made of plastic is clipped on the crossbeams 4. A left intermediate layer 10A has a left centering flank 10C, which extends around the holding structure 1 on the left (cf. FIGS. 5A and 10A, B). A right intermediate layer 10B correspondingly has a right centering flank 10C, which extends around the holding structure 1 on the right. The two centering flanks 10C together center the fastening device 3 in the lateral direction at the holding structure 1. The elastic centering flanks 10C have a spacing that is slightly smaller than the corresponding outside dimension of the holding structure 1, so that they are prestressed in the mounted state and thus center the fastening device on the holding structure.

The fastening device 3, which is obtained by plugging together the crossbeams and longitudinal beams, is fastened to a medical instrument (not shown) by means of screws 11.

To move the two longitudinal beams 5 relative to one another, a bolt 12A is screwed into a square nut 12B, which is arranged in the left longitudinal beam 5A in such a way that it is secured against rotation, passes through a hole in the right longitudinal beam 5B and is secured by a locking ring 12C in front of a bolt head against being pulled out. The bolt head presses in the opposite direction a head support formed in the right longitudinal beam 5B. When the bolt is rotated via a hexagon socket 12D, which is accessible laterally from the outside, the longitudinal beams move correspondingly towards each other or away from each other.

A medical instrument is fastened to the holding structure according to FIG. 1A or 1B as follows: The longitudinal beams and crossbeams 4, 5 as well as the intermediate layers 10 are first plugged into one another to form the fastening device 3, which is subsequently screwed onto the medical instrument by means of the screws 11.

Figure 5A:
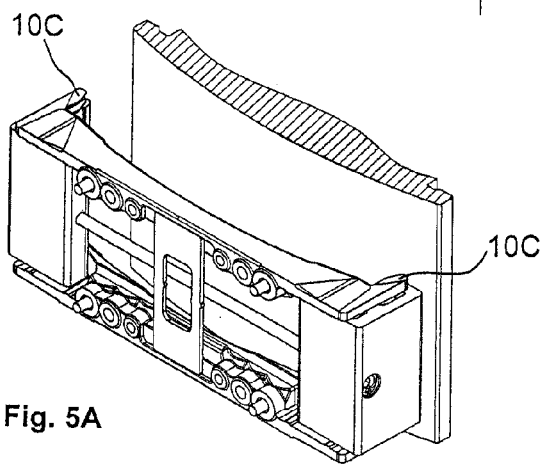
FIG. 5A is a perspective partial cross sectional view showing the fastening device according to FIG. 3 in the unfastened state.
Figure 7A:
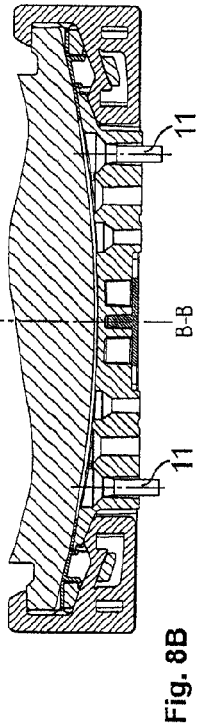
FIG. 7A is a cross sectional view along line A-A in FIG. 6A showing the fastening device according to FIG. 3 in the unfastened state.
Figure 7B:
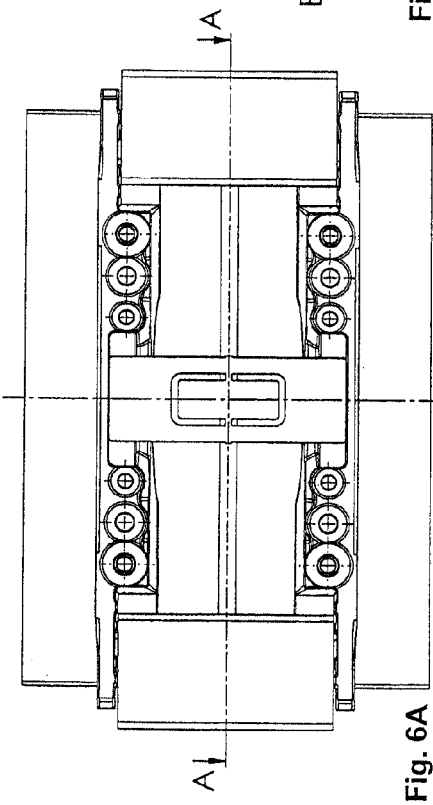
FIG. 7B is a cross sectional view along line B-B in FIG. 6B showing the fastening device according to FIG. 3 in the unfastened state.
Figure 8A:
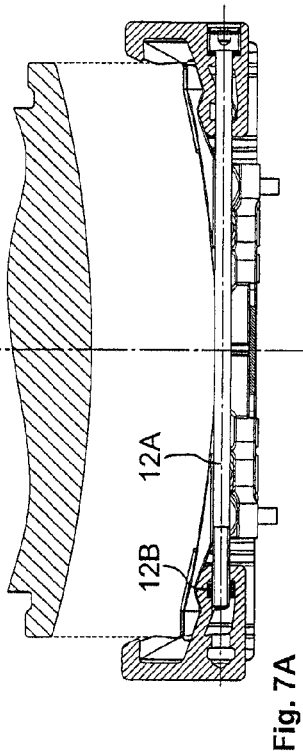
FIG. 8A is a cross sectional view along line A-A in FIG. 6A showing the fastening device according to FIG. 3 in the fastened state.
Figure 8B:
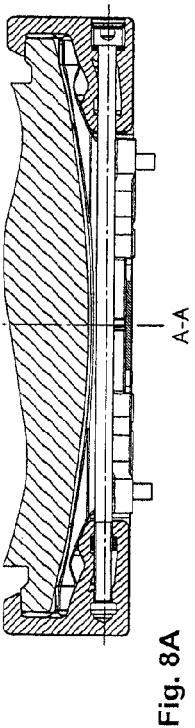
FIG. 8B is a cross sectional view along line B-B in FIG. 6B showing the fastening device according to FIG. 3 in the fastened state.

The fastening device 3 is now placed from the front on the holding structure 1 (cf. FIGS. 5A, 7). Bolt 12A is subsequently screwed into the closing direction. The longitudinal beams 5A, 5B move towards one another as a result, and their claws 6 extend behind the outer holding surfaces 1A of the holding device. At the same time, the crossbeams 4 are moved in the direction of the clamping surfaces 1B or 1C by the guide, i.e., the tongue-and-groove mimic 7, 8 and the surface pairs 9.

As soon as the intermediate layers 10 are in contact with the clamping surfaces 1B or 1C, a torque applied to bolt 12A in the closing direction braces the claws 6 and the surface pairs 9 against each other, so that the holding structure is clamped between the longitudinal beams and crossbeams and the fastening device 3 and with it the medical instrument are thus fixed to the holding structure 1 in a frictionally engaged manner.

Figure 5B:
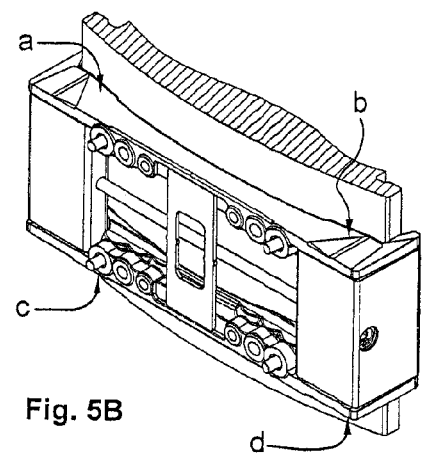
FIG. 5B is a perspective partial cross sectional view showing the fastening device according to FIG. 3 in the fastened state.
Figure 6A:
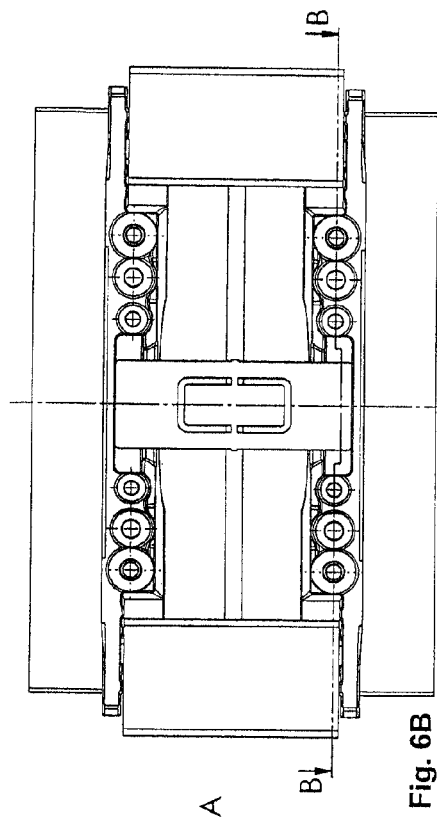
FIG. 6A is a front view of the fastening device according to FIG. 3 with the section lines A-A.
Figure 6B:
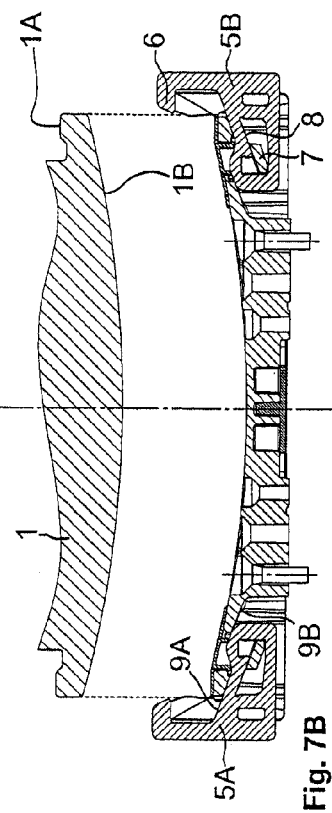
FIG. 6B is a front view of the fastening device according to FIG. 3 with the section lines B-B.

The torque applied laterally to the one bolt 12A thus advantageously brings about a uniform distribution of the normal and frictional forces, which act between the two crossbeams 4 and the two clamping surfaces 1B or 1C, among four action sites a-d (cf. FIG. 5B). An advantageous flow of forces is thus obtained between the medical instrument and the holding structure. To make it possible to fasten different medical instruments with the same fastening device to the holding structure, additional holes 11A with different diameters are provided, through which screws with a different nominal bore diameter and in a different position can be screwed in instead of screws 11 (cf. FIG. 3).

The axis of bolt 12A and hence the line of force of the tensile force exerted by said bolt is eccentric to the surface pairs 9. The overturning moment resulting from this is, however, supported well due to the relatively great distance between the respective surface pairs.

Mounting and removal, which takes place in the reversed order of the above-described steps, are advantageously very simple. For fastening, the medical instrument must only be placed from the front on the holding structure and a single, laterally arranged and hence readily accessible bolt must subsequently be tightened. When putting on, the centering flanks 10C secure correct lateral positioning of the fastening device 3 at the holding structure 1, and the fastening device is centered automatically by the subsequent relative motion of the longitudinal beams 5.

Figure 4:
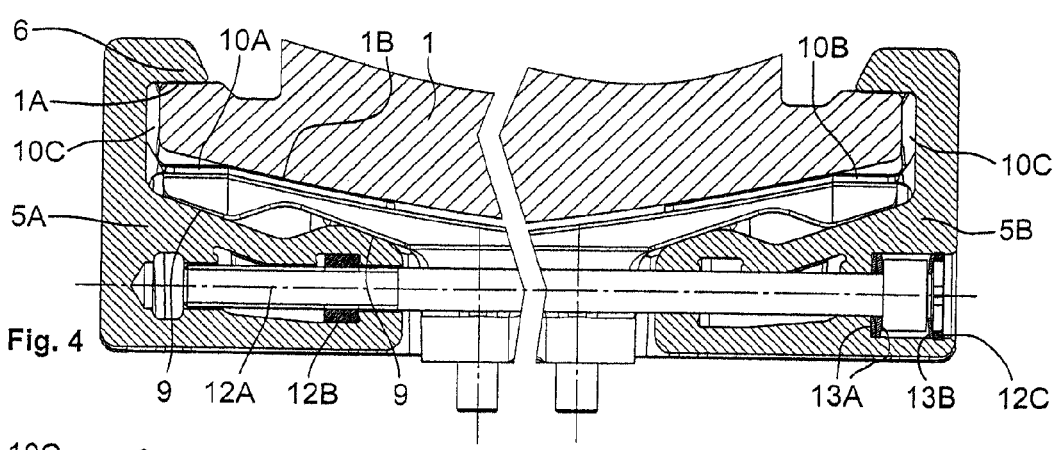
FIG. 4 is a cross sectional view showing an enlarged detail from FIG. 8A.

To prevent the bolt 12A from becoming loose, a securing means is provided in the form of two plate springs 13A, which are arranged in opposite directions and are inserted between the head support and the bolt head. Another plate spring 13B of the same type between the bolt head and the locking ring 12C improves the transmission of forces during the loosening of the fastening device (FIG. 4).

FIGS. 9A, 9B and 9C show a mounting means in the form of a three-part plastic bridge part 14, which comprises a frame part 14A (cf. FIG. 9C), a middle part 14B arranged therein in such a way that it can be broken off (cf. FIG. 9B) and an inner part 14C, which is in turn arranged therein in such a way that it can be broken off (cf. FIG. 9A). The frame part, middle part and inner part have a pin 14D each (cf. FIG. 3) at their upper and lower ends, which said pin is not shown in FIGS. 9A, 9B and 9C and can mesh with a corresponding recess 14E in a crossbeam 4A or 4B. Fastening devices of different overall heights can be preassembled with a mounting means which is adaptable in height in this manner.

As is seen especially in this exemplary embodiment, a fastening device according to the present invention can be advantageously adapted to medical instruments of different heights. Regardless of the height selected, the prestressing force of the clamping means can be distributed homogeneously among four or optionally also only two action sites and a favorable flow of forces can thus be preset.

FIGS. 10A and 10B show a cross section of an instrument system according to the first embodiment of the present invention in a top view. The two instrument systems differ in the contour of their holding structure 1; they correspond to those shown in FIGS. 2A and 2B.

As is shown by the comparison of FIGS. 10A and 10B, the same fastening device 3 can be fastened to different holding structures 1. The contour of the crossbeams 4 and the intermediate layers 10 of the fastening device 3 can be designed for this in the first embodiment such that it is complementary to the different clamping surfaces 1B and 1C of the different holding structures. The crossbeams 4 have for this purpose a curved surface 15 as well as plane faces 16 adjoining same laterally. If the fastening device 3 is mounted on a holding structure 1 according to FIG. 2A, the plane faces 16 are pressed against the clamping surfaces 1B thereof (FIG. 10A). If the fastening device 3 is mounted, by contrast, on a holding structure 1 according to FIG. 2B, the curved surface 15 contacts the complementarily curved clamping surface 1C thereof (FIG. 10B). This makes possible the fastening of the same fastening device 3 or of the medical instrument connected thereto to different holding structures.

Figure 11:
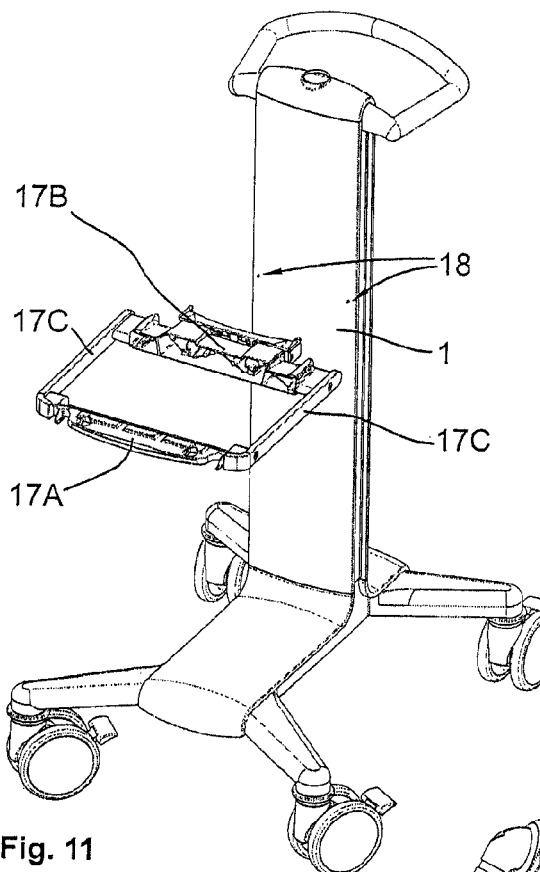
FIG. 11 is a perspective view showing the instrument system according to the first embodiment of the present invention in a first step of mounting.

FIG. 11 shows the instrument system according to the first embodiment of the present invention in a first step of mounting. The support frame 17, which comprises a rear part 17B facing the holding structure 1, a front part 17A located opposite hereto and two side parts 17C connecting these, is fastened in this embodiment in a first step of mounting to the holding structure 1 by means of a fastening device 3 according to the first embodiment. The fastening device 3 is first attached here by means of the lower edge of the lower crossbeam 4B to two positioning pins 18, which are located on the surface of the holding structure 1, before the crossbeams and claws of the fastening device fix the fastening device 3 and with it the support frame 17 to the holding structure 1 in a frictionally engaged manner.

Figure 12:
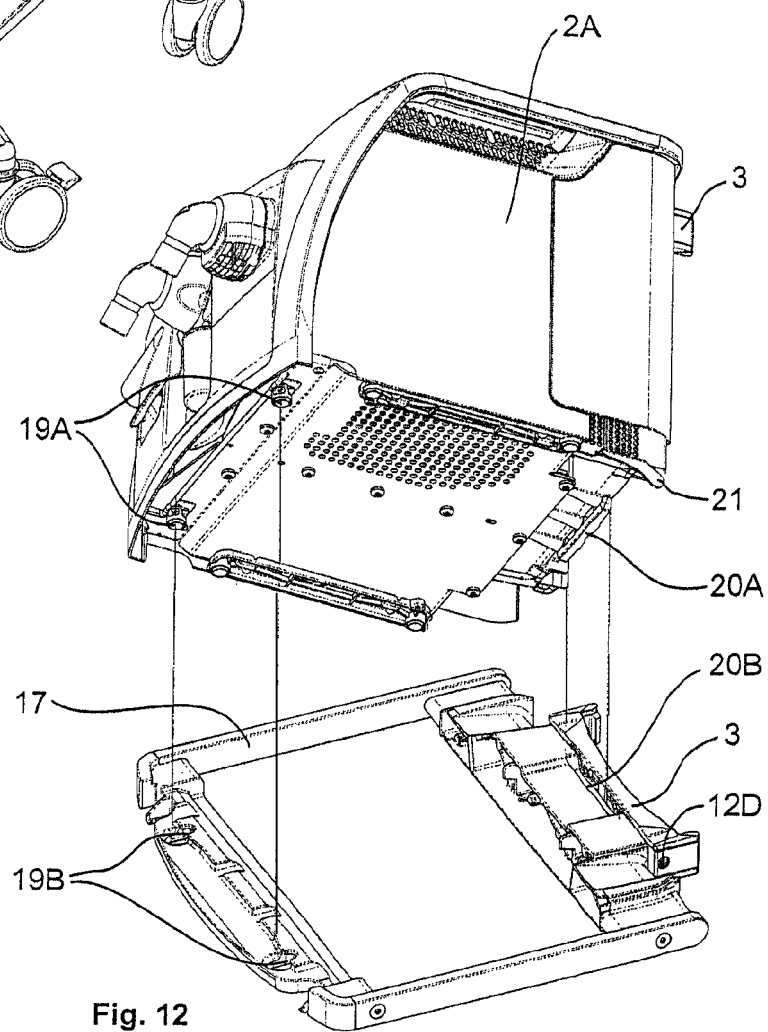
FIG. 12 is an exploded perspective view showing the instrument system according to the first embodiment of the present invention in a second step of mounting.

FIG. 12 shows a second step of mounting, in which the respirator 2A is placed from the top on the support frame 17 and is displaced rearwardly. Two front pins with recesses 19A of the respirator 2A mesh at first with corresponding receiving links 19B on the top side of the support frame 17. If the instrument is now displaced rearwardly, pins 19A enmesh with the receiving links 19B and a rear tongue 20A of respirator 2A will finally mesh with a complementary groove 20B, which is formed in support frame 17. Respirator 2A is subsequently fixed to the holding structure 1 by means of a fastening device 3, which is screwed onto the respirator 2A from behind in the vicinity of the upper edge of the respirator 2A. This holding structure has the standardized height of 0.5 h=40 mm (cf. FIG. 9A). Respirator 2A and support frame 17 now form a stable unit, which is fixed to the holding structure 1 in a frictionally engaged manner with two fastening devices 3 spaced far apart from each other, so that the weight of the respirator 2A and the torque resulting herefrom are well supported.

At the same time, the support frame is supported in the front area by the positive-locking connection between pin 19A and the receiving links 19B at the respirator in the vertical loading direction. The additional weight of additional accessories, which can be arranged at the side parts 17C, which are designed as standard rail sections—especially, e.g., an articulated arm—is thus well supported.

To prevent the respirator 2A from being able to drop off accidentally during removal as well, the hexagon socket 12D of the clamping element of the fastening device 3, with which the support frame 17 is fastened to the holding structure 1, is blocked by a blocking means having a sheet metal tongue 21 arranged at the respirator 2A. It is ensured hereby that the fastening device 3 of the respirator 2A is first released and this instrument is lifted off from the support frame 17 before the fastening device 3 of the support frame 17 can be released.

FIG. 13 and FIG. 16 show a third step of mounting. For illustration, the respirator 2A mounted in the preceding, second step is blanked out in FIG. 13 and FIG. 16. A medical instrument in the form of a humidifier 2B has, on its top side, front hooks 22A and rear hooks 22B, which are shown in an enlarged form in the detail views in FIGS. 14 and 15. These hooks extend into front hooks 23A and rear hooks 23B, respectively, which are shown in an enlarged form in the detail view in FIGS. 17 and 18, when the humidifier 2B is pushed in on the underside of support frame 17.

After the humidifier 2B has been pushed in completely under the support frame 17, it is fastened with a fastening device 3 according to the present invention to the holding structure 1 in a frictionally engaged manner. Based on the small height of the humidifier 2B, the fastening device 3 of said humidifier 2B is manufactured with the standardized height h=80 mm (cf. FIG. 9A).

Figure 19:
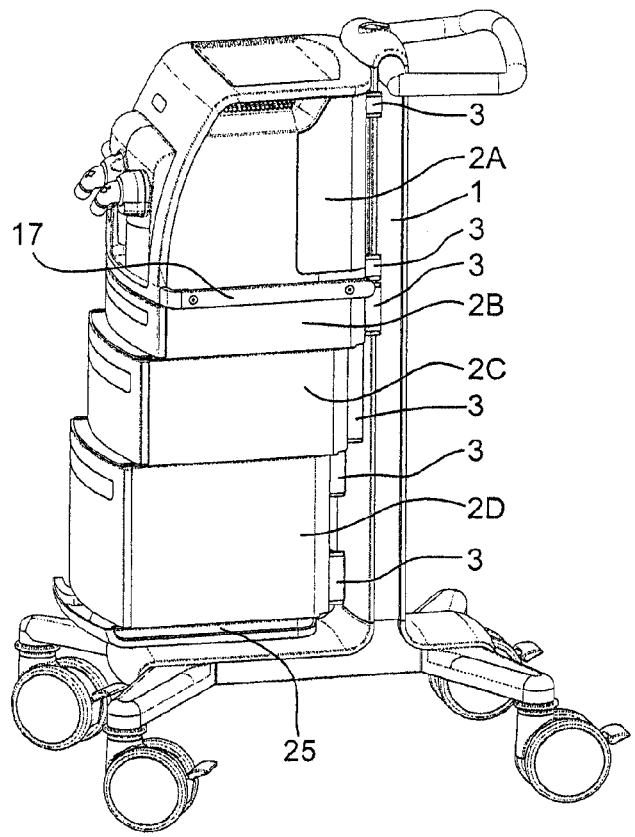
FIG. 19 is a perspective view showing the instrument system according to the first embodiment of the present invention in a fourth step of mounting.

In a fourth step of mounting shown in FIG. 19, the pressure source 2C is pushed in on the underside of the humidifier 2B and the independent power supply unit 2D is pushed in successively on the underside of the pressure source 2C. The individual medical instruments have hooks 22A, 22B for this on their top side, as they were described above in reference to the humidifier 2B. On their underside, the medical instruments have two hooks 23A, 23B, as they were described above in reference to the support frame 17 (cf. FIG. 20). The instruments can thus be arranged beneath the support frame 17 in any desired order, and each instrument is fastened to the holding structure 1 by means of a fastening device 3 before the next instrument is suspended on its underside. In addition or as an alternative, it is also possible to provide medical instruments like the respirator 2A described above, which can be connected to a support frame or to another medical instrument only on their underside or only on their top side and correspondingly have no hook arrangement on their top side and on their underside and are preferably of a smooth design.

The heavy respirator 2A advantageously does not have to be held by the user during fastening to the holding structure 1, i.e., during the clamping of the clamping element, because it is supported on the support frame 17. In the same manner, the medical instruments 2B-2D arranged under the support frame 17 also do not have to be supported by the user during fastening to the holding structure 1, because they are held through the hook arrangement 22, 23 by the superjacent support frame 17 or medical instrument. This facilitates mounting and prevents the instruments from falling off accidentally during mounting and removal.

To achieve the greatest possible distance of the action sites and hence good support of the torques resulting from the weights, the pressure source 2C, which is higher than the humidifier 2B, is fastened with a fastening device 3 at the standardized height 2h=160 mm (cf. FIG. 9C). The independent power supply unit 2D is fastened with two fastening devices 3 at the standardized height h=80 mm, which are screwed on at the upper and lower edges of the battery 2D and have a distance of h=80 mm.

Figure 20:
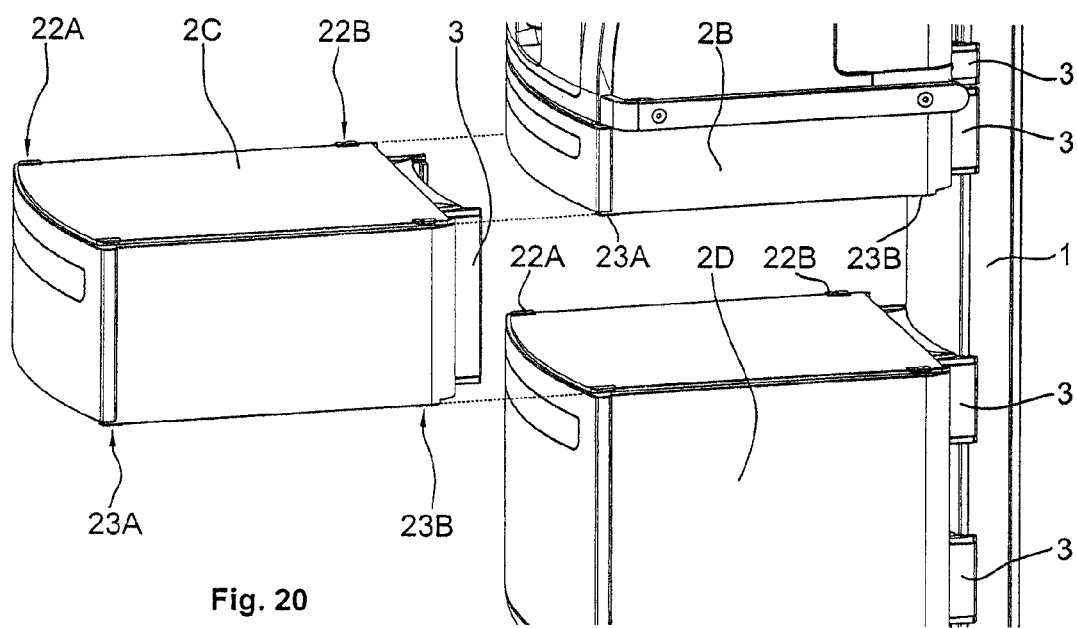
FIG. 20 is a perspective partial view showing the instrument system according to the first embodiment of the present invention during the subsequent mounting or removal of a medical instrument.

As is shown in FIG. 20, individual medical instruments can be removed in a simple manner by detaching first the particular fastening device 3 from the holding structure 1 and subsequently pulling out the medical instrument from the instrument system in the forward direction. The hook arrangement 22, 23 on the top side and the underside of the medical instruments is correspondingly designed such that it permits pushing in and pulling out in the forward direction.

A free underside of the support frame 17 or of a lowermost medical instrument is connected by a hook arrangement 23, 24 to a closing element 25 (FIGS. 21 through 23). Since this carries no load, it is not fastened to the holding structure with a fastening device in order to save material. In order to nevertheless prevent the closing element 25 from sliding out in the forward direction, the hooks 24 of closing element 25 have a locking mechanism, for example, a dog or detent or a spring-loaded catch. They otherwise correspond to the hooks 22 on the top side of the medical instruments 2. Instead of a medical instrument, it is consequently also possible to push a closing element 25 under the underside of support frame 17 or of a lowermost medical instrument. This instrument is locked with its front hook 24A and rear hook 24B with the front and rear hooks 23A, 23B, respectively, on the underside of support frame 17 or of the lowermost medical instrument. FIG. 21 shows a corresponding closing element 25 from the top, and FIGS. 22, 23 show detail views of the hooks 24A, 24B with a locking mechanism, which can interlock with the hooks 23A and 23B, respectively, on the underside of support frame 17 or of a medical instrument. Elastic dogs 26A arranged in the front are elastically deformed for this when the hooks 23 are pushed into the hooks 24 and equalize the clearance between the hooks, so that rattling is counteracted. In addition, elastic locking tongues 26B arranged in the rear can snap into corresponding recesses 23C of the rear hooks 23B (cf. FIG. 18 and FIG. 28).

FIG. 24 shows the instrument system according to the first embodiment of the present invention according to another modification, which now comprises two drawers 2E without support frame. As in the modified first exemplary embodiment according to FIG. 1B, the top side of a topmost medical instrument has here a hook arrangement, which shall not be exposed. A closing element 25 is therefore likewise fastened on the top side of the topmost medical instrument. As is shown in FIG. 1B and FIG. 24, this is advantageously designed as a depositing tray.

As can be recognized from FIG. 25 and from the detail views in FIGS. 26 and 27, closing element 25 has a hook arrangement 27, which can be pushed into the hooks 22 on the top side of the topmost medical instrument and can be locked with these, as this was already explained, in principle, in connection with the closing element of the first embodiment according to FIG. 21.

In order to make it possible to use a closing element 25 both to cover a top side and an underside of the support frame 17 or of a medical instrument, side parts 25A of the closing element 25 have, on a first longitudinal side (top in FIG. 21, bottom in FIG. 25), a hook arrangement 24, which can be caused to mesh with the hook arrangement 23 on the underside of the medical instruments. On a second longitudinal side located opposite the first one (bottom in FIG. 21, top in FIG. 25), they have a hook arrangement 27, which can be caused to mesh with the hook arrangement 22 on the top side of the medical instruments. By transposing the side parts 25A, either the first or the second longitudinal side with the corresponding hook arrangement 24, 27 is exposed and meshes the hook arrangement on the underside and the top side of the support frame or medical instrument when the closing element 25 is pushed in on the underside or on the top side of a support frame or medical instrument.

Consequently, the two side parts 25A, which are screwed onto the closing element, are detached, turned by 180° about their longitudinal side and screwed on again on the opposite side of the closing element in order to convert the closing element according to FIG. 21, which is provided for fastening on the underside of the support frame or of a medical instrument, into the closing element according to FIG. 25, which is provided for fastening on the top side of the support frame or of a medical instrument. The closing elements for the top side and the underside can thus be manufactured or converted one into the other from the same components in a simple manner, which lowers the manufacturing effort and the stocking costs.

The hook geometries used to fasten the closing elements can be integrated either directly in the housing parts or designed as repeatedly reusable standardized individual parts, for example, as zinc diecastings.

If standardized individual parts are used, this is possible, for example, in the form shown in FIG. 28. Only two different embodiments are advantageously necessary here, namely, upper hooks 22 and lower hooks 23. Four pieces of each of these two embodiments may be used, as is shown in FIG. 28. Especially in case of device components of a small overall height (e.g., 1 h), upper hooks and lower hooks arranged corresponding to each other can be integrated into one component each.

FIGS. 29 and 30 show a hook 22 and a hook 23 each from FIG. 28 in enlarged views. It can be recognized here that the hooks may have notches 22C and 23C, respectively, which can be used for snapping in the closing element 25, which is not shown in FIGS. 28 through 30.

Figure 31:
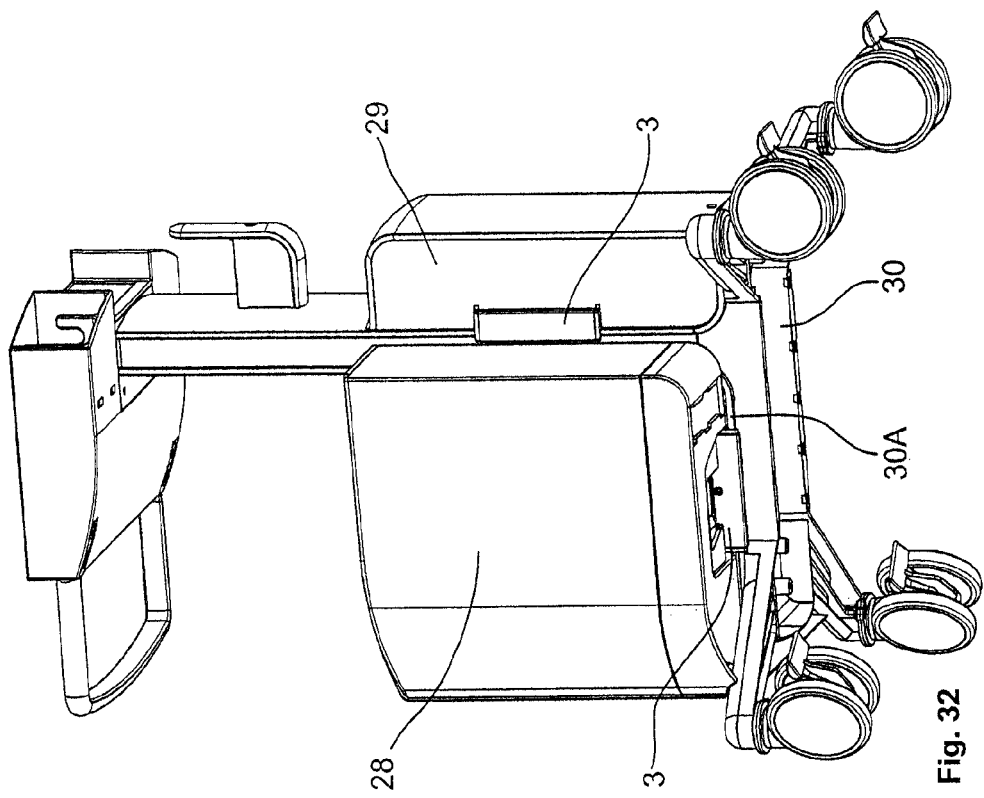
FIG. 31 is a lower perspective view (shown in a removed state) showing another possible use of a fastening device according to the present invention for fastening a compressor housing and a battery housing to a trolley.
Figure 32:
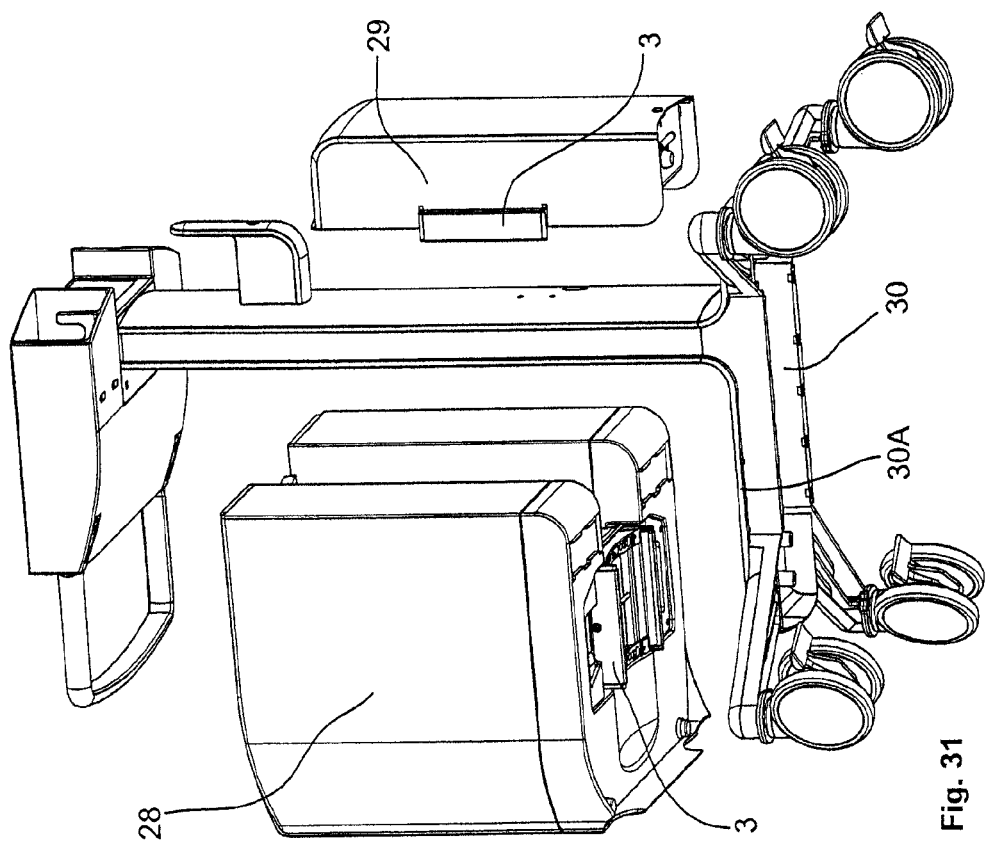
FIG. 32 is a lower perspective view showing another possible use of a fastening device according to the present invention for fastening a compressor housing and a battery housing to a trolley.

FIGS. 31 and 32 show another, possible use of a fastening device according to the present invention for fastening a compressor housing 28 and a battery housing 29 on a trolley. FIG. 31 shows a state before the mounting of the compressor housing 28 and of the battery housing 29, and FIG. 32 shows a state after the mounting thereof on the trolley.

A fastening device 3 with h=160 mm in the horizontal position is used to mount the compressor housing 28 and is screwed to a horizontal strut 30A designed with the section of the holding structure 1 shown in FIG. 2B at a trolley foot 30 of the trolley. Providing only one screw that is to be tightened is advantageous for a fastening in which screws that are to be tightened are provided in a poorly accessible location, as in case of the use shown in FIG. 31 and FIG. 32.

A battery housing 29 is likewise fastened to the trolley with a fastening device 3 with h=160 mm. Since the section of the vertical holding structure 1 of the trolley is the same on the front side and the rear side thereof, the battery housing 29 could alternatively also be placed on the front side of the trolley instead of the mounting arrangement shown in FIG. 32 on the rear side of the trolley.

FIG. 33 shows a gas cylinder holder 31 fastened to a trolley by means of the fastening device according to the present invention. FIG. 34 shows the gas cylinder holder 31 in a removed and disassembled state.

The gas cylinder holder 31 has an upper part 31A with clamping belts 32 and a lower part 31B with clamping belts 32 as well as footprint areas 33. The fastening device has a somewhat modified design: Unlike in the embodiment of the fastening device shown in FIGS. 3, 4 and 9, the complementary wedge surfaces 9B (see FIG. 35), on which the wedge surfaces 9A of the longitudinal beams 5A and 5B run, and contact surfaces (curved surface 15 and plane face 16) for the section of the holding structure 1 are formed, instead of by two crossbeams 4A, 4B, by an extruded section 34, which forms the base part of the gas cylinder holder 31. In addition, no plastic intermediate layers are provided here.

Tongues, which correspond to the oblique projections 7 according to FIG. 3, which are integrated in the clamping strip 4A, 4B, are made integrally in one piece on two covers 35 mounted from the top and from the bottom in the variant according to FIGS. 33 through 35. Their function is in turn the forced oblique guiding of the longitudinal beams during the opening and closing of the fastening device. They are, furthermore, end stops. Likewise integrated in the covers are right and left centering flanks 10C, which inevitably leads to central mounting.

FIG. 36 shows the result of the fastening of a horizontal 10×25-mm standard rail 36A on a fastening device hereinafter called a holder 36, which fastening is shown graphically in FIG. 37, in order to make it possible to fasten or adapt any desired accessories, e.g., humidifier, bronchial suction device or the like, by means of the standard rail 36A. The design embodiment of the "universal holder" thus formed differs from the above-described variants and will therefore be described in more detail below.

Holder 36 according to FIG. 36 has, as can be recognized in FIG. 37, a one-part crossbeam 37, in which two longitudinal beams 5A and 5B slide via oblique surface pairs 9A, 9B. A restrictedly guided oblique guiding is brought about by pins 38, which are inserted into the longitudinal beams 5A, 5B and slide on bevels 39. These bevels 39 are integrated, together with end stop faces 40, in a cover part 41, which completely surrounds the function site together with two plugs 41A. The longitudinal beams 5A, 5B are pulled or braced against each other by means of a bolt 42, which is firmly inserted into the longitudinal beam 5A, and a screw grip 43 screwed onto the bolt 42 by turning the screw grip 43. The use of the screw grip 43 makes it possible to mount and remove the holder 36 manually. The stressing of the claws is not released positively in this variant, but by two compression springs 44, which push off the longitudinal beams 5A, 5B from the crossbeam 37 in both directions when the screw connection is loosened. The standard rail section 36A screwed on from behind forms the interface for accessories.

Figure 38:
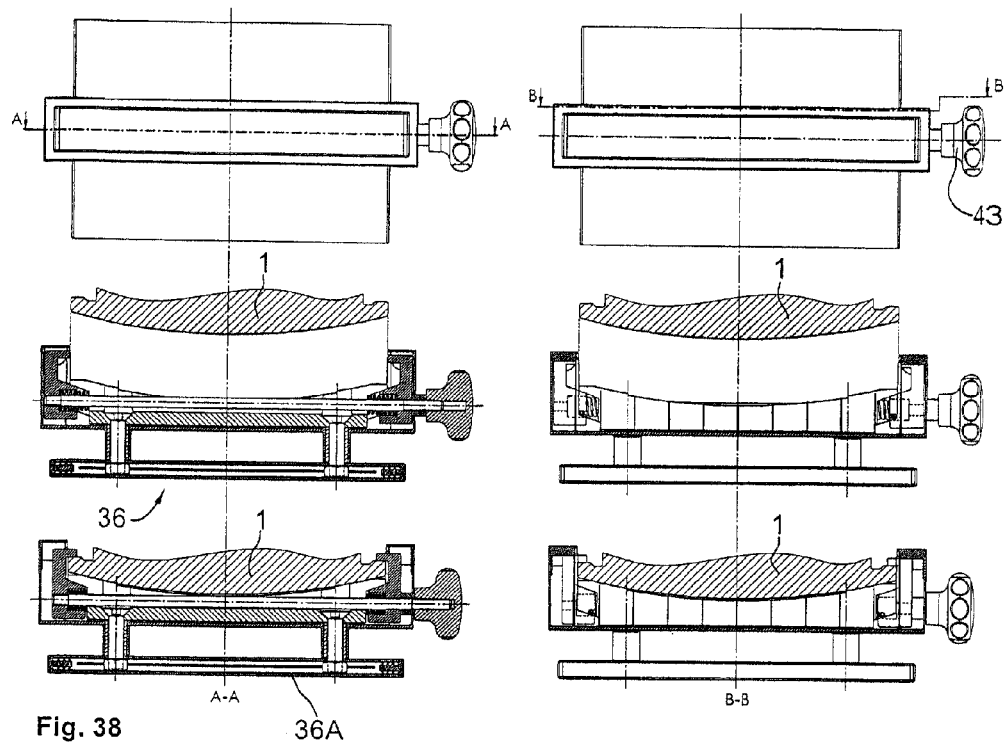
FIG. 38 is a series of views showing further details of the fastening device shown in FIGS. 36 and 37.
Figure 39:
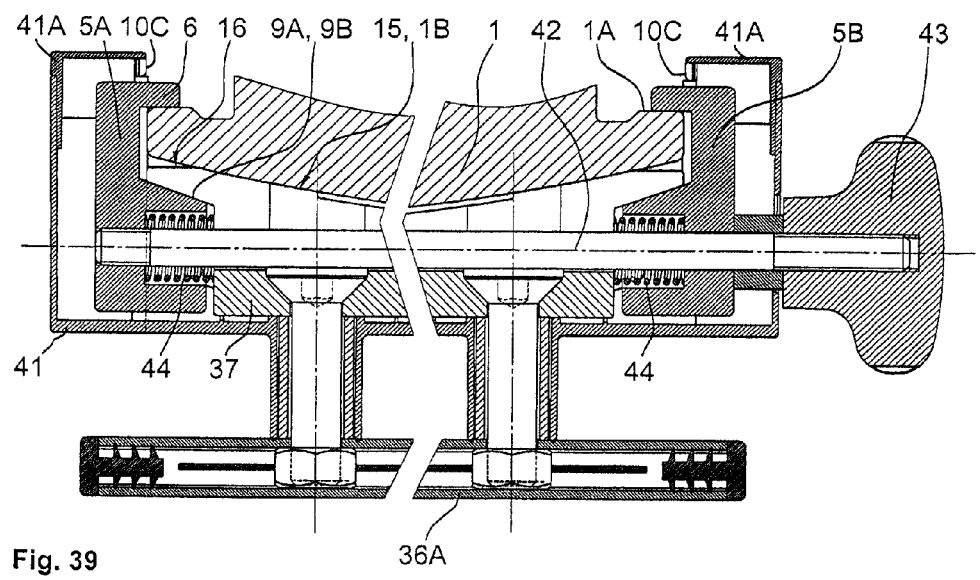
FIG. 39 is a sectional broken away view showing further details of the fastening device shown in FIGS. 36 and 37.

FIGS. 38 and 39 show further details of the fastening device shown in FIGS. 36 and 37. In the open state (see the upper sectional views in FIG. 38), holder 36 can be attached to the section of the holding structure 1 from the front, and right-side and left-side centering flanks 10C, which are integrated in the cover part 41 and the plug 41A, inevitably ensure central mounting. The screw grip 46 is subsequently screwed in the closing direction, so that claws 6 of the longitudinal beams 5A, 5B extend behind the holding surfaces 1A of the holding structure 1. Bolt 42 braces the two longitudinal beams 5A and 5B against each other when tightened, so that the crossbeam 37 is pressed directly against the section of the holding structure 1 due to the wedge effect on the surface pairs 9A, 9B and the abutment are the surface pairs between the curved surfaces 15 of crossbeam 37 and the clamping surface 1C.

The mechanism has a path reserve towards the inside in order for the wedge transmission to be able to become fully effective. Even though the line of force of bolt 42 is eccentric in relation to the surface pair 9A, 9B, the developing overturning moment acting on the longitudinal beams 5A, 5B, is counteracted by the compression springs 44, which are also provided for opening the mechanism. Two plane faces 16 provided at the outer ends of crossbeam 37 guarantee compatibility even with a holding structure 1B of the shape shown in FIG. 2A.

While specific embodiments of the invention have been shown and described in detail to illustrate the application of the principles of the invention, it will be understood that the invention may be embodied otherwise without departing from such principles.

LIST OF REFERENCE NUMBERS

1 Holding structure
1A Holding surface
1B Clamping surface, flat
1C Clamping surface, curved
2A Respirator
2B Humidifier
2C Pressure source
2D Independent power supply unit
2E Drawer
3 Fastening device
4A, 4B Crossbeam
5A, 5B Longitudinal beam
6 Claw
7 Oblique projections
8 Groove
9 Surface pair
9A Wedge surface
9B Complementary wedge surface
10A, 10B Intermediate layer
10C Centering flank
11 Screw
11A Hole
12A Bolt
12B Square nut
12C Locking ring
12D Hexagon socket
13A, 13B Plate springs
14 Plastic bridge part
14A Frame part
14B Middle part
14C Inner part
14D Pin
14E Recess
15 Curved surface
16 Plane face
17 Support frame
17A, 17B Front part, rear part
17C Side part
18 Positioning pin
19A Pin with recess
19B Receiving link for pin
20A Tongue on respirator
20B Complementary groove
21 Sheet metal tongue
22A, 22B Hooks on top side
22C Recess in hook on top side
23A, 23B Hooks on underside
23C Recess in hook on underside
24A, 24B Hooks on lower closing element
25 Closing element
26A Elastic dog
26B Elastic detent
27A, 27B Hooks on upper closing element
28 Compressor housing
29 Battery housing
30 Trolley foot
30A Horizontal bar
31 Gas cylinder holder
31A Upper part of gas cylinder holder
31B Lower part of gas cylinder holder
32 Clamping belt
33 Footprint area
34 Extruded section
35 Covers
36 Holder
36A Standard rail section
37 One-part crossbeam
38 Pin
39 Bevels
40 End stop faces
41 Cover part
41A Plug for closing part
42 Bolt
43 Screw grip
44 Compression spring

What is claimed is:

1. A fastening device for detachably fastening a medical instrument on a holding structure with a holding surface, and having two crossbeams, the fastening device comprising:
    two longitudinal beams with at least one claw for extending behind the holding surface of the holding structure;
    a first guide by which one of the two crossbeams are moved in a direction toward the claws of the longitudinal beams during a motion of the longitudinal beams in relation to one another;
    a second by which the other of the two crossbeams is moved in a direction toward the claws of the longitudinal beams during a motion of the longitudinal beams in relation to one another, the two crossbeams being on diametrically opposite sides of said two longitudinal beams; and
    a position changing means for changing the distance between the longitudinal beams in relation to one another including moving the longitudinal beams in relation to one another.

2. A fastening device in accordance with claim 1, wherein the claws are caused to engage the holding surfaces of holding structure by the motion of the longitudinal beams in relation to one another.

3. A fastening device in accordance with claim 1, wherein the guides comprise a surface pair with a wedge surface arrangement formed on said longitudinal beams and a complementary wedge surface arrangement formed on the one crossbeam, wherein wedge surfaces of the wedge surface arrangement and of the complementary wedge surface arrangement that touch each other form an angle with the direction of motion of the longitudinal beams.

4. A fastening device in accordance with claim 1, wherein said guides comprise a tongue-and-groove mimic with an oblique projection arranged on one of the longitudinal beams and the one crossbeam, and a recess formed on the other of the longitudinal beam and the one crossbeam, wherein the recess and the projection form an angle with the direction of motion of the longitudinal beams.

5. A fastening device in accordance with claim 1, wherein said position changing means comprises a clamping means accessible on a side to move the longitudinal beams in relation to one another.

6. A fastening device in accordance with claim 1, further comprising a centering means for positioning the fastening device in the direction of the two crossbeams.

7. A fastening device in accordance with claim 1, further comprising a positioning means for positioning said fastening device at the holding structure in the direction of the longitudinal beams.

8. An instrument system comprising:
   a holding structure with a holding surface;
   a medical instrument to be fastened to the holding structure; and
   a fastening device comprising two crossbeams, and comprising two longitudinal beams with at least one claw for extending behind the holding surface of the holding structure, a first guide, and a second guide, by which the two crossbeams are moved in a direction toward the claws of the longitudinal beams during a motion of the longitudinal beams in relation to one another and a position changing means for changing the distance between the longitudinal beams in relation to one another including moving the longitudinal beams in relation to one another, said two crossbeams being on diametrically opposite sides of said two longitudinal beams.

9. An instrument system in accordance with claim 8, wherein the claws are caused to engage the holding surfaces of holding structure by the motion of the longitudinal beams in relation to one another.

10. An instrument system in accordance with claim 8, wherein the guides comprise a surface pair with a wedge surface arrangement formed on said longitudinal beams and a complementary wedge surface arrangement formed on the crossbeams, wherein wedge surfaces of the wedge surface arrangement and of the complementary wedge surface arrangement that touch each other form an angle with the direction of motion of the longitudinal beams.

11. An instrument system in accordance with claim 8, wherein said guides comprise a tongue-and-groove mimic with an oblique projection arranged on one of the longitudinal beams and one of the crossbeams, and a recess formed on the other of the longitudinal beam and other one of the crossbeams, wherein the recess and the projection form an angle with the direction of motion of the longitudinal beams.

12. An instrument system in accordance with claim 8, wherein said position changing means comprises a clamping means accessible on a side to move the longitudinal beams in relation to one another.

13. An instrument system in accordance with claim 8, further comprising a centering means for positioning the fastening device in a direction of the crossbeams.

14. An instrument system in accordance with claim 8, further comprising a positioning means for positioning said fastening device at the holding structure in the direction of the longitudinal beams.

15. An instrument system in accordance with claim 8, further comprising a support frame fastened by said fastening device to said holding structure, said medical instrument being fastened to said support frame.

16. An instrument system according to claim 15, wherein said medical instrument has a hook arrangement for fastening to one or more of another medical instrument, to a support frame and to a closing element.

17. An instrument system according to claim 12, wherein said medical instrument further comprises a blocking means for blocking said clamping means of said fastening device, by which another medical instrument arranged directly under said medical instrument or a support frame is fastened to said holding structure.

18. A fastening device in accordance with claim 1, wherein:
   said position changing means moves said first and second longitudinal beams toward each other in a direction perpendicular to the direction toward said claws;
   said guides move the crossbeams in the direction toward the claws of the longitudinal beams during motion of the longitudinal beams in the direction perpendicular to the direction toward said claws.

19. An instrument system in accordance with claim 8, wherein:
   said position changing means moves said first and second longitudinal beams toward each other in a direction perpendicular to the direction toward said claws;
   said guides move the crossbeams in the direction toward the claws of the longitudinal beams during motion of the longitudinal beams in the direction perpendicular to the direction toward said claws.

20. A fastening device for detachably fastening a medical instrument on a holding structure with a holding surface and with a clamping surface arranged on a diametrically opposite sides of said holding structure, the fastening device comprising:
   first and second longitudinal beams, each of said longitudinal beams having a claw adapted to be positioned against the holding surface, each of said longitudinal beams being adapted to extend from said claw and around the holding structure to said clamping surface,
   a first crossbeam arrangable on the clamping surface side of the holding structure, said crossbeam being connected to said first and second longitudinal beams;
   a variable connector connected to said first and second longitudinal beams, said variable connector selectively moving said first and second longitudinal beams toward each other in a direction along the clamping surface;
   a first guide arranged between said crossbeam and said first and second longitudinal beams, said guide forcing said crossbeam toward said claws and against the clamping surface when said variable connector moves said first and second longitudinal beams toward each other in the direction along the clamping surface;
   a second crossbeam arrangable on the clamping surface side of the holding structure, said another crossbeam also being connected to said first and second longitudinal beams, said crossbeam and said another crossbeam being on diametrically opposite sides of said first and second longitudinal beams;
   a second guide arranged between said another crossbeam and said first and second longitudinal beams, said another guide forcing said another crossbeam toward said claws and against the clamping surface when said variable connector moves said first and second longitudinal beams toward each other in the direction along the clamping surface.

21. A fastening device in accordance with claim 20, wherein:
said guides include sliding surfaces on said crossbeams and said longitudinal beams, said sliding surfaces being arranged to have said sliding surfaces on said longitudinal beams force said sliding surfaces on said crossbeams toward said claws and the holding surface when said variable connector moves said first and second longitudinal beams toward each other.

22. A fastening device in accordance with claim 1, wherein:
said guides move said one of the two crossbeams in a direction against said clamping surface during motion of said longitudinal beams toward each another.

23. An instrument system in accordance with claim 8, wherein:
said guide move said two crossbeams in a direction against said clamping surface during motion of said longitudinal beams in relation toward each another.

* * * * *